(12) United States Patent
Bell et al.

(10) Patent No.: US 9,249,419 B2
(45) Date of Patent: Feb. 2, 2016

(54) NON-RECOMBINANT SACCHAROMYCES STRAINS THAT GROW ON XYLOSE

(75) Inventors: Philip John Livingstone Bell, New South Wales (AU); Paul Victor Attfield, New South Wales (AU)

(73) Assignee: Microbiogen Pty Ltd., Sydney, New South Wales (AU)

( * ) Notice: Subject to any disclaimer, the term of this patent is extended or adjusted under 35 U.S.C. 154(b) by 0 days.

(21) Appl. No.: 13/589,864

(22) Filed: Aug. 20, 2012

(65) Prior Publication Data

US 2013/0065270 A1    Mar. 14, 2013

Related U.S. Application Data

(62) Division of application No. 11/570,329, filed as application No. PCT/AU2005/000824 on Jun. 8, 2005, now Pat. No. 8,257,959.

(30) Foreign Application Priority Data

Jun. 8, 2004  (AU) ................................ 2004903141

(51) Int. Cl.
| | |
|---|---|
| C12N 1/18 | (2006.01) |
| C12N 15/01 | (2006.01) |
| C12N 15/81 | (2006.01) |
| C12P 7/06 | (2006.01) |
| C12R 1/865 | (2006.01) |
| C12R 1/85 | (2006.01) |

(52) U.S. Cl.
CPC ................. *C12N 15/81* (2013.01); *C12N 1/18* (2013.01); *C12N 15/01* (2013.01); *C12P 7/06* (2013.01); *C12R 1/85* (2013.01); *C12R 1/865* (2013.01); *Y02E 50/17* (2013.01)

(58) Field of Classification Search
CPC .................... C12N 1/18; C12R 1/865
See application file for complete search history.

(56) References Cited

U.S. PATENT DOCUMENTS

| 4,368,268 | A | 1/1983 | Gong |
| 4,396,632 | A | 8/1983 | Clement et al. |
| 4,511,656 | A | 4/1985 | Gong |
| 5,741,695 | A | 4/1998 | Hennette et al. |
| 6,071,729 | A | 6/2000 | Jeffries et al. |
| 6,716,631 | B1 | 4/2004 | del Cardayre et al. |
| 7,253,001 | B2 | 8/2007 | Wahlbom et al. |
| 7,531,348 | B2 | 5/2009 | Cordero Otero et al. |
| 2003/0157675 | A1 | 8/2003 | Cordero Otero et al. |
| 2004/0077090 | A1 | 4/2004 | Short |

FOREIGN PATENT DOCUMENTS

| EP | 0066396 A1 * | 8/1982 | ................. C12P 7/06 |
| EP | 0066396 | 8/1985 | |
| EP | 0511108 | 4/1992 | |
| EP | 1007732 | 7/2006 | |
| JP | 1979-35280 | 8/1977 | |
| JP | A-S61-242584 | 10/1986 | |
| JP | A-S64-065679 | 3/1987 | |
| JP | 1994-178682 | 12/1992 | |
| JP | 2003-250523 | 9/2003 | |
| RU | 2186846 | 8/2002 | |
| RU | 2208630 | 7/2003 | |
| WO | 98/31784 | 7/1998 | |
| WO | 00/04190 | 1/2000 | |
| WO | 2007/018442 | 2/2007 | |
| WO | 2007/121100 | 10/2007 | |
| WO | 2009/155633 | 12/2009 | |

OTHER PUBLICATIONS

Attfield and Bell, "Genetics and classical genetic manipulations of industrial yeasts" Topics in Genetics vol. 2, J.H. Winde (Ed.); Functional Genetics of Industrial Yeasts, Springer Verlag, Berlin, Heidelberg (2003).

Attfield et al., "Use of population genetics to derive nonrecombinant *Saccharomyces cerevisiae* strains that grow using xylose as a sole carbon source," FEMS Yeast Res. 6:862-868 (2006).

Batt et al., "Direct evidence for a xylose metabolic pathway in *Saccharomyces cerevisiae*" Biotech. Bio. Eng., 28(4):549-553 (1986).

Becker et al., "A Modified *Saccharomyces cerevisiae* Strain That Consumes L-Arabinose and Produces Ethanol" App. Environ. Microbiol., 4144-4150 (2003).

Cebollero et al., "Comparison of Two Alternative Dominant Selectable Markers for Wine Yeast Transformation" App. Environ. Microbiol., 70(12):7018-7023 (2004).

Chiang et al., "Ethanol production from pentoses by immobilized microorganisms" Enz. Micro. Tech. 4(2):93-95 (1982).

Delgenes et al., "Effects of Lignocellulose Degradation Products on Ethanol Fermentations of Glucose and Xylose by *Saccharomyces cerevisiae, Zymomonas mobilis, Pichia stipitis*, and *Candida shehatae*," Enzyme and Microbial Technology, 19:220-225 (1996).

Dobson et al., "The identification and high level expression of a protein encoded by the yeast Ty element" Embo J. 3:1115-1119 (1984).

Eliasson et al., "Anaerobic Xylose Fermentation by Recombinant *Saccharomyces cerevisiae* Carrying XYL1, XYL2, and XKS1 in Mineral Medium Chemostat Cultures" App. Environ. Microbiol. 66:3381-3386 (2000).

Fowell, "Sporulation and hybridization of yeast" in the Yeasts (A.H. Roase and J.S. Harrison, eds.) Academic Press (1969).

(Continued)

*Primary Examiner* — Renee Claytor
*Assistant Examiner* — Michelle F Paguio Frising
(74) *Attorney, Agent, or Firm* — Occhiuti & Rohlicek LLP

(57) ABSTRACT

The present invention relates to methods for producing *Saccharomyces* strains that are capable of growth on xylose as a sole carbon source at a desired growth rate, (such as at least one generation per 48 hours), strains made by such methods, and *Saccharomyces* strains that grow at a growth rate of at least one generation per 48 hours using xylose as a sole carbon source for growth made by non-recombinant methods.

18 Claims, 1 Drawing Sheet

(56) References Cited

OTHER PUBLICATIONS

Gong et al., "Conversion of pentoses by yeasts" Biotech. Bio. Eng. 25(1):85-102 (1983).

Hagerdal et al., "Metabolic Engineering of *Saccharomyces cerevisiae* for xylose utilization", Advances in Biochemical Engineering/Biotechnology, vol. 73, pp. 53-84 (2001).

Hahn-Hagerdal et al. "Towards industrial pentose-fermenting yeast strains," Appl Microbiol Biotechnol. 74:937-953 (2007).

Heluane et al., "Characterization of hybrids obtained by protoplast fusion, between *Pachysolen tannophilus* and *Saccharomyces cerevisiae*," App. Microbiol. And Biotech. Springer Verlag, Berlin, DE, vol. 40, No. 1, pp. 98-100, (1993).

Herbert et al., "Chemical Analysis of Microbial Cells," Methods in Microbiol. vol. 5B (Eds. J.R. Norris and D.W. Ribbons), Chapter III pp. 209-344, Academic Press London and New York (1971).

Higgins et al., "Generation of a novel *Saccharomyces cerevisiae* strain that exhibits strong maltose utilization and hyperosmotic resistance using nonrecombinant techniques" Appl. Env. Microbiol., 67:4346-4348 (2001).

Higgins et al., "Genetic evidence that high noninduced maltase and maltose permease activities, governed by MALx3-encoded transcriptional regulators, determine efficiency of gas production by baker's yeast in unsugared dough" Appl. Env. Microbiol., 65:680-685 (1999).

Ho et al., "Genetically Engineered Saccharomyces Yeast Capable of Effective Cofermentation of Glucose and Xylose", Appl. Environ. Microbiol. 64:1852-1859 (1998).

Inge-Vechtomov et al., "Hybridization of cells of the same mating type in *Saccharomyces* yeasts" Genetika 22:2625-2636 (1986).

Johansson and Hahn-Hagerdal, "The Non-oxidative Pentose Phosphate Pathway Controls the Fermentation Rate of Xylulose but not of Xylose in *Saccharomyces cerevisiae* TMB3001" FEMS Yeast Res. 2:277-282 (2002).

Jeppsson et al., "Reduced Oxidative Pentose Phosphate Pathway Flux in Recombinant Xylose-Utilizing *Saccharomyces cerevisiae* Strains Improves the Ethanol Yield from Xylose," Applied and Environmental Microbiology, 68:1604-1609 (2002).

Johnston, in Yeast Technology, Spencer JFT and Spencer DM (Eds.) Springer Verlag, New York (1990).

Karhumaa et al., "Investigation of limiting metabolic steps in the utilization of xylose by recombinant *Saccharomyces cerevisiae* using metabolic engineering" Yeast 22:359-368 (2005).

Katahira et al., "Ethanol fermentation from lignocellulosic hydrolysate by a recombinant xylose- and cellooligosaccharide-assimilating yeast strain," Appl Microbiol Biotechnol 72:1136-1143 (2006).

Kordowksa et al., "Application of *Saccharomyces cerevisiae* and *Pichia stipitis* karyoductants to the production of ethanol from xylose," Acta Microbiologica Polonica, vol. 50, Nos. 3-4, pp. 291-299 (2001).

Kouno et al., "Separation of Pentose-Utilizing Yeasts" (English Translation), Annual Report of Industrial Technology Center of Okayama Prefecture, No. 21, pp. 19-21 (1995).

Kurtzman, "Phylogenetic circumscription of *Saccharomyces, Kluyveromyces* and other members of the *Saccharomycetaceae*, and the proposal of the new genera Lachancea, Nakaseomyces, Naumovia, Vanderwaltozyma and Zygotorulaspora" FEMS Yeast Res. 4:233-245 (2003).

Kurtzman, "Phylogenetic relationships among yeasts of the 'Saccharomyces complex' determined from multigene sequence analyses" FEMS Yeast Res. 3:417-432 (2003).

Kuyper et al., "High-level functional expression of a fungal xylose isomerase: the key to efficient ethanolic fermentation of xylose by *Saccharomyces cerevisiae*?" FEMS Yeast Res. 4(1):69-78 (2003).

Kuyper et al., "Minimal metabolic engineering of *Saccharomyces cerevisiae* for efficient anaerobic xylose fermentation: a proof of principle," FEMS Yeast Res., Elsevier Science Tokyo, NL, vol. 4, No. 6, pp. 655-664 (2004).

Lebeau et al., "Fermentation of D-xylose by free and immobilized *Saccharomyces cerevisiae*" Biotech Letts. 19(7):615-618 (1997).

Lindegren," Selecting, Inbreeding, Recombining, and Hybridizing Commercial Yeasts" J. Bacteriology 46:405-419 (1943).

Lowry et al., "Protein measurement with the Folin phenol reagent" J. Biol. Chem. 193:265-275 (1951).

Morgan, "Yeast strain improvement by protoplast fusion and transformation," Experientia Suppl. 46:155-166 (1983).

Ohgren et al., "Simultaneous saccharification and co-fermentation of glucose and xylose in steam-pretreated corn stover at high fiber content with *Saccharomyces cerevisiae* TMB3400", J. Biotech., vol. 126, No. 4, pp. 488-498 (2006).

Olsson et al., "Fermentation of lignocellulosic hydrolysates for ethanol production," Enzyme and Microbial Technology 18: 312-331 (1996).

Polaina et al., "Self-diploidization in *Saccharomyces cerevisiae* kar2 heterokaryons" Current Genetics 24:369-372 (1993).

Pretorius, "Tailoring wine yeast for the new millenium: novel approaches to the ancient art of wine making" Yeast 16:675-729 (2000).

Richard et al., "Evidence that the gene YLR070c of *Saccharomyces cerevisiae* encodes a xylitol dehydrogenase," FEBS Letts., 457(1): 135-138 (1999).

Sonderegger et al., "Evolutionary engineering of *Saccharomyces cerevisiae* for anaerobic growth on xylose" Appl. Environ. Microbiol. 69:1990-1998 (2003).

Sonderegger et al., "Fermentation Performance of Engineered and Evolved Xylose-Fermenting *Saccharomyces cerevisiae* Strains," Biotechnology and Bioengineering, 87:90-98 (2004); Article first published online: Jun. 11, 2004, DOI: 10.1002/bit.20094.

Sonderegger et al., "Metabolic Engineering of a Phosphoketolase Pathway for Pentose Catabolism in *Saccharomyces cerevisiae*", Appl. Environ. Microbiol. 70:2892-2897 (2004).

Sutherland et al., "Chemical Extraction Methods of Microbial Cells" Methods in Microbiology vol. 5B (Eds. J.R. Norris and D.W. Ribbons), Chapter IV, pp. 345-383, Academic Press, London and New York (1971).

Van Zyl et al., "D-Xylose Utilization by *Saccharomyces cerevisiae*", J. Gen. Microbiol. 135:2791-2798 (1989).

Volfová et al., "Selection of a yeast strain with optimal utilization of straw hydrolyzates," Folia Microbiologica, vol. 24, No. 2, pp. 157-162 (1979).

Wahlbom et al., "Generation of the improved recombinant xylose-utilizing *Saccharomyces cerevisiae* TMB 3400 by random mutagenesis and physiological comparison with Pichia stipitis CBS 6054" FEMS Yeast Res. 3(3):319-326 (2003).

Wahlborn et al., "Molecular analysis of a *Saccharomyces cerevisiae* mutant with improved ability to utilize xylose shows enhanced expression of proteins involved in transport, initial xylose metabolism, and the pentose phosphate pathway" Appl. Environ. Microbiol. (2):740-746 (2003).

Johnston and Oberman, "Yeast Genetics in Industry," Bull M.J. (Ed.), Progress in Industrial Microbiology, Elsevier, Amsterdam, 15:151-205 (1979).

Kuyper et al., "Evolutionary engineering of mixed-sugar utilization by a xylose-fermenting *Saccharomyces cerevisiae* strain," FEMS Yeast Res. 5:925-934 (2005).

Liu et al., "Continuous fermentation of hemicellulose sugars and cellulose to ethanol," International Symposia on Alcohol Fuels, 1-28 (2005).

Persson et al., "Effect of different forms of alkali treatment on specific fermentation inhibitors and on the fermentability of lignocellulose hydrolysates for production of fuel ethanol," J. Agric. Food Chem. 50:5318-5325 (2002).

\* cited by examiner

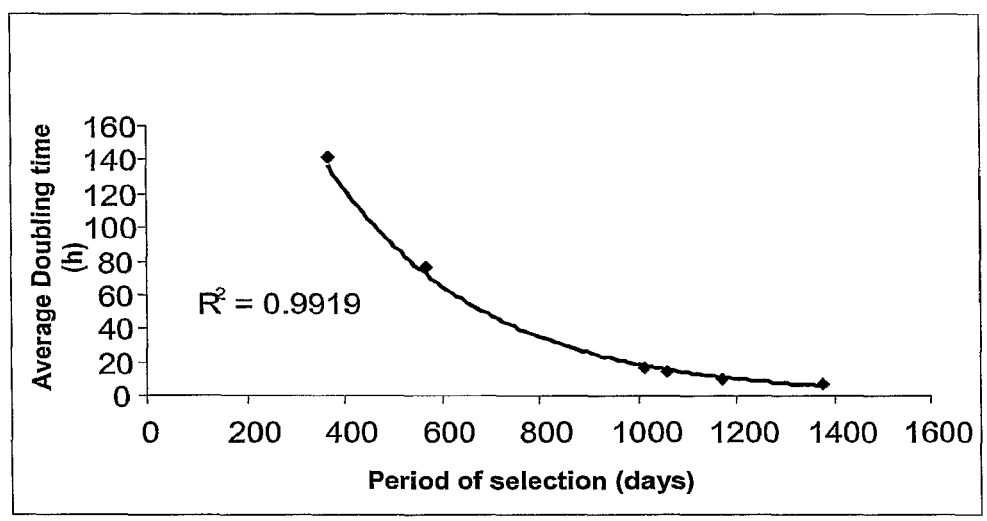

NON-RECOMBINANT SACCHAROMYCES STRAINS THAT GROW ON XYLOSE

This application is a divisional application of, and claims the benefit of priority under 35 U.S.C. §121 of, U.S. application Ser. No. 11/570,329, filed Dec. 8, 2006, which is a U.S. national phase application of International Application No. PCT/AU2005/000824, filed Jun. 8, 2005, which claims priority from Australian Application Serial No. 2004903141, filed Jun. 8, 2004. The entire content of these applications is hereby incorporated by reference herein.

FIELD OF THE INVENTION

The invention relates to methods for producing non-recombinant strains of *Saccharomyces*, strains of *Saccharomyces*, and uses thereof.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

One of the most important economic groups of yeasts are of the genus *Saccharomyces*, strains of which are employed in the brewing, baking, winemaking, distilling and various other yeast-dependent industries. Species of *Saccharomyces* are as defined phylogenetically by Kurtzman (2003) FEMS Yeast Research 3:417-432, and include *S. cerevisiae, S. paradoxus, S. mikatae, S. cariocanus, S. kudriavzevii, S. pastorianus* and *S. bayanus*.

*Saccharomyces* spp. are some of the most effective microorganisms for converting sugars such as glucose, fructose, sucrose and maltose to biomass, and for fermenting these sugars to ethanol. As a consequence, *Saccharomyces* spp., and in particular *Saccharomyces cerevisiae*, is one of the most widely used microorganisms in industrial processes. For example, in the beer brewing, distilling and wine industries, *Saccharomyces* are used to ferment sugars such as glucose, fructose, sucrose and/or maltose into ethanol. In the fuel ethanol industry, *Saccharomyces cerevisiae* strains are chosen for their ability to rapidly convert high concentrations of sugars such as glucose, fructose, sucrose and maltose into high amounts of ethanol. In the baking industry, *Saccharomyces cerevisiae* strains are used primarily for their ability to produce carbon dioxide from sugars such as glucose, fructose, sucrose, and/or maltose in order to leaven bread. Other applications of *Saccharomyces cerevisiae* include production of yeast extracts and other flavour and aroma products, sources of enzymes such as invertase, production of various biochemicals, intermediates, proteins, amino acids, ribonucleic acid and nucleotides co-factors and vitamins.

Millions of tonnes of yeast are grown each year in industrial processes. Therefore, the ability of *Saccharomyces* to grow on abundant and renewable carbon sources is important in terms of economic production of yeast biomass for industrial purposes and for economic production of byproducts from yeast metabolism. In particular the ability of *Saccharomyces* to grow on waste byproducts of other industrial processes is of environmental and economic value. Thus, for example, baker's yeast biomass is often produced by growing yeast on molasses which is a waste product of the sugar production process, or on glucose- and maltose-rich syrups derived from starch hydrolysis industry.

SUMMARY OF THE INVENTION

The invention provides methods of producing a *Saccharomyces* strain that is capable of growing at a desired growth rate (such as at least one generation per 48 hours), using xylose as a sole carbon source, and strains of *Saccharomyces* that grow on xylose under these growth rates, and the uses thereof.

Xylose is an example of a naturally occurring, abundant and renewable sugar available from plant biomass that *Saccharomyces* was previously considered not able to use. See for example, Barnett et al. 'Yeasts Characteristics and Identification' 2nd edition (1990), Cambridge University Press, which states that yeast of the species *Saccharomyces cerevisiae* are not capable of utilizing xylose as a sole carbon source for growth. Xylose represents a major potential source for growing yeasts and for manufacturing products, including ethanol, from yeasts. The use of xylose as a sugar source for yeasts would provide major economic and environmental advantages. For example, production of fuel ethanol from xylose-rich materials would be a major source of renewable energy.

In a first aspect, the invention provides a method of producing a *Saccharomyces* strain that is capable of growing at a desired growth rate using xylose as a sole carbon source for growth, comprising:
 (a) providing a population of genetically diverse non-recombinant yeast cells of *Saccharomyces*;
 (b) culturing the yeast cells under conditions which permits combining of DNA between yeast cells;
 (c) screening or selecting the yeast cells for yeast cells which have increased growth rate using xylose as a sole carbon source for growth;
 (d) isolating one or more yeast cells which have the desired growth rate.

Typically, the yeast cells are cultured under conditions which permit combining of DNA between pairs of yeast cells.

Typically, the desired growth rate is an increase in growth rate relative to that of yeast cells of *Saccharomyces* strains to which the method has not been applied. For example, Saccharomyces strains such as strain NL67. More typically, the desired growth rate is at least one generation per 48 hours, more typically at least one generation per 24 hours.

Typically, the yeast cells are screened or selected for yeast cells which have the desired growth rate by incubating the yeast cells in or on xylose-containing medium. Typically, the xylose-containing medium is xylose-containing culture medium. The culture medium may contain xylose as the only carbon source, or xylose may be one of a plurality of carbon sources. Typically, the xylose is the only carbon source in the xylose-containing medium. Typically, the xylose-containing culture medium is xylose minimal mineral media. The yeast cells are typically incubated on or in the xylose-containing medium for sufficient time to permit yeast cells having the desired growth rate using xylose as a carbon source to grow.

In one embodiment, the screened or selected yeast cells form the population of genetically diverse non-recombinant yeast cells, and steps (b) and (c) are repeated until yeast cells having the desired growth rate are obtained.

In one embodiment, step (b) is performed prior to step (c). In another embodiment, step (c) is performed before step (b). In yet another embodiment, steps (b) and (c) are performed simultaneously.

In a second aspect, the invention provides a method of producing a *Saccharomyces* strain in culture that is capable of a desired growth rate using xylose as a sole carbon source for growth, comprising:
(a) providing a population of genetically diverse non-recombinant yeast cells of *Saccharomyces*;
(b) culturing the yeast cells under conditions which permits combining of DNA between yeast cells;
(c) screening or selecting the yeast cells by incubating the yeast cells on or in a xylose-containing medium;
(d) repeating steps (b) and (c) with the screened or selected cells forming the population of genetically diverse non-recombinant yeast cells of *Saccharomyces*, until one or more yeast cells have acquired the ability to grow at a desired growth rate using xylose as a sole carbon source for growth.

Typically, the method comprises the further step (e) of isolating one or more yeast cells having the desired growth rate. In one embodiment, the one or more yeast cells that is isolated is a single strain of *Saccharomyces*. In another embodiment, the one or more yeast cells that is isolated is a population of genetically diverse yeast cells.

In one embodiment, the yeast cells are selected in step (c). The yeast cells may be selected in step (c) by incubating the yeast cells on or in xylose-containing medium for sufficient time to permit yeast cells capable of growth on xylose as a sole carbon source to grow using xylose as the carbon source, and thereafter collecting the yeast cells that grow. The yeast cells may be selected in step (c) by incubating the yeast cells on or in xylose-containing medium for sufficient time to permit yeast cells having an increased growth rate using xylose as a sole carbon source to grow using xylose as the carbon source, and thereafter collecting the yeast cells that grow.

In another embodiment, the yeast cells are screened in step (c). The yeast cells may be screened in step (c) by incubating the yeast cells on or in xylose-containing medium for sufficient time to permit yeast cells having an increased growth rate using xylose as a sole carbon source to grow using xylose as the carbon source, and thereafter collecting the yeast cells that have an increased growth rate using the xylose as a carbon source.

It is also envisaged that in a portion of the repeats of steps (b) and (c), the yeast cells will be selected, and in a portion of the repeats of steps (b) and (c), the yeast cells will be screened.

Steps (b) and (c) may be repeated any number of times that is sufficient to obtain a yeast strain that is capable of growth at the desired rate using xylose as a sole carbon source for growth. It will be appreciated by persons skilled in the art that the number of times that steps (b) and (c) will be repeated will depend upon the medium which is used, the starting yeast strains, the culturing conditions, etc. In one embodiment, steps (b) and (c) are repeated at least once, typically at least 2 times, more typically at least 5 times, even more typically at least 10 times, still more typically at least 20 times, suitably at least 30 times.

The yeast cells may be screened or selected on solid or in liquid xylose-containing medium. In one embodiment, the cells are screened or selected on solid xylose-containing medium. In another embodiment, the cells are screened or selected in liquid xylose-containing medium. In yet another embodiment, the cells are screened or selected on solid xylose-containing medium, followed by screening or selection in liquid xylose-containing medium. For example, the yeast cells may be screened or selected for a plurality of times by repeating steps (b) and (c) using solid xylose-containing medium, followed by screening or selection for a plurality of times by repeating steps (b) and (c) using liquid xylose-containing medium.

The solid xylose-containing medium may be any solid medium that contains xylose as a carbon source, and which provides a selective advantage to a strain that is capable of utilising xylose as a sole carbon source. For example, the solid xylose-containing medium may be a complex solid medium in which xylose is one of a plurality of carbon sources, or the solid xylose-containing medium may be a minimal solid medium in which xylose is the sole carbon source. Typically, the solid xylose-containing medium will be solid minimal medium containing xylose as a sole carbon source.

The liquid xylose-containing medium may be any liquid medium that contains xylose as a carbon source. For example, the liquid xylose-containing medium may be a complex liquid medium in which xylose is one of a plurality of carbon sources, or the liquid xylose-containing medium may be a minimal liquid medium in which xylose is the sole carbon source. Typically, the liquid xylose-containing medium will be liquid minimal medium containing xylose as a sole carbon source. Typically, the liquid minimal medium is minimal mineral medium containing xylose as a sole carbon source.

The desired growth rate is typically at least one generation per 48 hours. The desired growth rate may be greater than one generation per 24 hours. The desired growth rate may be greater than one generation per 12 hours. The desired growth rate may be greater than one generation per 10 hours. The desired growth rate may be greater than one generation per 8 hours. The desired growth rate may be greater than one generation per 4 hours. The desired growth rate may be greater than one generation per 2 hours.

The *Saccharomyces* strain that is produced may be a strain from any species of the genus *Saccharomyces* that is capable of growth at a desired growth rate using xylose as a sole carbon source for growth. It will be appreciated by those skilled in the art that the strain that is produced will depend on the species which form the genetically diverse population of non-recombinant yeast cells of *Saccharomyces*. Examples of suitable species of yeast include *S. cerevisiae*, *S. paradoxus*, *S. mikatae*, *S. cariocanus*, *S. kudriavzevii*, *S. pastorianus* and *S. bayanus*. Typically the strain is of the species *Saccharomyces cerevisiae*. Typically the strain will be capable of mating with *Saccharomyces* of the same species. Typically the strain will be capable of mating with *Saccharomyces cerevisiae*.

The yeast may be cultured under any conditions which permit combining of DNA between yeast cells provided the combining of DNA is not by recombinant methods. The yeast cells may be cultured under conditions which permit combining of DNA between yeast cells by, for example, mating or cytoduction, or any other methods known in the art for combining of DNA of yeast cells, other than recombinant methods. In one embodiment, the yeast cells are cultured under conditions which permit mating of the yeast cells. Typically, mating of yeast comprises sporulating the yeast to produce spores, germinating the spores, and mating the germinated spores. Methods for mating yeast are known to those skilled in the art and are described in, for example, Fowell (1969) "Sporulation and hybridization of yeast", in, The Yeasts (A H Rose and J S Harrison, eds.), Academic Press; European Patent EP 0 511 108 B; Attfield and Bell (2003) "Genetics and classical genetic manipulations of industrial yeasts" in, Topics in Current Genetics, Vol 2. Functional Genetics of Industrial Yeasts (J. H. de Winde, ed.), Springer-Verlag Berlin Heidelberg or combinations thereof.

The population of genetically diverse non-recombinant yeast cells may be naturally-occurring isolates of *Saccharomyces* from any source, spontaneously mutated isolates of *Saccharomyces*, or may be obtained by exposing one or more *Saccharomyces* strains to a mutagen. The population of genetically diverse non-recombinant yeast cells may be strains from a single species, or may be strains from a plurality of species. Species suitable for use as the genetically diverse population of non-recombinant yeast cells includes *S. cerevisiae, S. paradoxus, S. mikatae, S. cariocanus, S. kudriavzevii, S. pastorianus* and *S. bayanus*. Typically the strains are of the species *Saccharomyces cerevisiae*. Typically the strains are capable of mating with *Saccharomyces* of the same species. Typically the strains are capable of mating with *Saccharomyces cerevisiae*.

It will be understood by persons skilled in the art that in addition to the population of genetically divergent non-recombinant yeast cells, recombinant yeast cells may be included in steps (b) and (c) as a separate population.

In a third aspect, the invention provides a method of generating a derivative of a *Saccharomyces* strain with an increased growth rate using xylose as a sole carbon source for growth, comprising:
  (a) providing yeast cells of the strain as a portion of a population of genetically diverse yeast cells of *Saccharomyces;*
  (b) culturing the population of genetically diverse non-recombinant yeast cells of *Saccharomyces* under conditions which permits combining of DNA between the yeast cells of the population;
  (c) screening or selecting yeast cells for derivatives of the strain that have an increased growth rate on xylose;
  (d) isolating one or more derivatives of the strain which have an increased growth rate using xylose as a sole carbon source for growth relative to the growth rate of the strain using xylose as a sole carbon source for growth.

The yeast cells are typically screened or selected by incubating the yeast cells on or in xylose-containing medium.

In one embodiment, the yeast cells are selected in step (c). The yeast cells may be selected in step (c) by incubating the yeast cells on or in xylose-containing medium for sufficient time to permit yeast cells capable of growth on xylose as a sole carbon source to grow using xylose as the carbon source. The yeast cells may be selected in step (c) by incubating the yeast cells on or in xylose-containing medium for sufficient time to permit yeast cells having an increased growth rate using xylose as a sole carbon source to grow using xylose as the carbon source.

In another embodiment, the yeast cells are screened in step (c). The yeast cells may be screened in step (c) by incubating the yeast cells on or in xylose-containing medium for sufficient time to permit yeast cells having an increased growth rate using xylose as a sole carbon source to grow using xylose as the carbon source, and thereafter collecting the yeast cells that grow fastest using the xylose as a carbon source.

Steps (b) and (c) may typically be repeated, whereby the derivatives form at least a portion of the population of genetically diverse *Saccharomyces* strains, until one or more derivatives have acquired an increased growth rate on xylose as a sole carbon source for growth.

In the past, to address the problem of the inability of *Saccharomyces cerevisiae* to use xylose, others have used recombinant DNA approaches to introduce genes obtained from yeast which can utilise xylose as a carbon source to confer on *Saccharomyces* the ability to utilise xylose (eg. Sonderegger and Sauer (2003) Applied and Environmental Microbiology 69: 1990-1998). In these approaches, the genes for xylose utilisation have been cloned from organisms which are capable of utilising xylose for growth, and subsequently introduced into *Saccharomyces cerevisiae*. For example, fungal xylose isomerase from *Piromyces* spp. has been integrated into the genome of *Saccharomyces cerevisiae* to generate strains which grow slowly on xylose as a sole carbon source (Kuyper et al. 2003). Xylose reductase from *Pichia stipitis* has also been cloned into *Saccharomyces cerevisiae* to generate yeast that can utilise xylose as a sole carbon source for growth (Wahlbom et al. 2003).

Non-recombinant *Saccharomyces cerevisiae* is "generally regarded as safe" (GRAS) and if recombinant techniques are used to develop *Saccharomyces cerevisiae* that utilize xylose, they lose the GRAS status. It is therefore not necessarily industrially or economically useful, desirable, or suitable to use strains of *Saccharomyces cerevisiae* that contain genes from other genera or species, or that are produced using recombinant DNA methods. Indeed strains that are derived through recombinant DNA approaches are not industrially useful where there are socio-, or enviro-political or other barriers to use of such strains.

The use of recombinant DNA techniques reduces the opportunities and desirability to use yeasts in human foods etc., whereas non-recombinant strains could be advantageously used for human foods etc. The ability to use non-recombinant yeast simultaneously for ethanol and for human foods provides opportunities to improve cost-efficiencies of yeast-based processes. For example it is possible to use non-recombinant yeasts to convert xylose to ethanol and yeast biomass. The ethanol may be used for fuel and other applications whereas the yeast produced may be used in other valuable applications such as production of extracts or other by-products.

The inventors have found that when non-recombinant wild-type strains of *Saccharomyces* are incubated on medium comprising xylose as a sole carbon source, very slow growth on the xylose is detectable. This is contrary to the prior art, which clearly indicates that *Saccharomyces* is not capable of growth on xylose. The inventors believe that the growth of *Saccharomyces* on xylose is so slow that it has not been previously detected. As described herein, the inventors have found that when solid minimal mineral medium containing xylose as a sole carbon source was inoculated with wild-type strains of *Saccharomyces cerevisiae*, growth was detectable by microscopic examination of colonies following incubation for 2 months at 30° C. Although the detectable growth allowed application of non-recombinant strategies to be used to derive yeast with improved growth rates, the observed very slow growth rate does not have industrial utility.

The inventors have extended their finding that *Saccharomyces* is capable of very slow growth on xylose as a sole carbon source to develop strains of *Saccharomyces* that are capable of growth on xylose as a sole carbon source at much higher rates than strains of *Saccharomyces* to which the method of the present invention has not been applied. Prior to the inventors finding, it was not thought possible that incubating yeast cells of *Saccharomyces* in or on medium containing xylose as sole carbon source would result in any selection or enrichment of yeast cells which were capable of growth on xylose as it was believed that the yeast would not grow in the medium because xylose was seen as a non-useable carbon source for *Saccharomyces*. Nevertheless, by using their findings and a combination of selection strategies and methods such as mating of populations of genetically diverse strains of *Saccharomyces*, suitably strains of *Saccharomyces cerevisiae*, the inventors have found that *Saccharomyces* strains can be produced that are capable of growth on solid medium, and/or in liquid medium, containing xylose as a sole carbon source at rates that are higher than those of *Saccharomyces* strains to which methods of the present invention have not been applied. Moreover, the inventors have found that by employing selection strategies and methods such as mating of genetically diverse strains of *Saccharomyces*, *Saccharomyces* strains can be produced that have a growth rate using xylose as a sole carbon source that is at least one generation per 48 hours, and in some advantageous embodiments, may be greater than one generation per 4 hours. Thus, by using non-recombinant methods, the inventors have been able to generate *Saccharomyces* strains that are capable of growth in liquid and on solid media containing xylose as a sole carbon source at industrially useful rates.

In a fourth aspect, the invention provides a *Saccharomyces* strain produced by the method of the first to third aspects of the invention.

In an fifth aspect, the invention provides an isolated *Saccharomyces* strain which is capable of a growth rate of at least one generation per 48 hours using xylose as a sole carbon source for growth, wherein the strain produces:
  (i) a 5-fold increase in biomass when grown under the conditions specified in Test T1; and
  (ii) at least 10 mg dry weight of biomass when grown under the conditions specified in Test T2,
  and wherein the strain is produced by the method of the first to third aspects.

In a sixth aspect, the invention provides an isolated *Saccharomyces* strain which is capable of a growth rate of at least one generation per 48 hours using xylose as a sole carbon source for growth, wherein:
  (i) the strain produces a 10-fold increase in biomass when grown under the conditions specified in Test T1; and
  (ii) the strain produces at least 50 mg dry weight of biomass when grown under the conditions specified in Test T2; and
  (iii) at least 0.1 g/l of ethanol is detected under the conditions specified in Test T3; and
  (iv) at least 1 nanomole of NAD(P)H is reduced or oxidised per minute per mg of protein extract at 30° C. under the conditions specified in Test T4; and
  (v) at least 1 nanomole of NAD(P)H is reduced or oxidised per minute per mg of protein extract at 30° C. under the conditions specified in Test T5; and
  wherein the strain is produced by the method of the first to third aspects.

In an seventh aspect, the invention provides an isolated *Saccharomyces* strain which is capable of a growth rate of at least one generation per 48 hours using xylose as a sole carbon source for growth, wherein:
  (i) the strain produces at least a 5-fold increase in biomass when grown under the conditions specified in Test T1; and
  (ii) the strain produces at least 40 mg dry weight of biomass when grown under the conditions specified in Test T2; and
  (iii) at least 1 nanomole of NAD(P)H is reduced or oxidised per minute per mg of protein extract at 30° C. under the conditions specified in Test T4; and
  (iv) at least 1 nanomole of NAD(P)H is reduced or oxidised per minute per mg of protein extract at 30° C. under the conditions specified in Test T5; and
  (v) the strain produces at least a 5-fold increase in biomass under the conditions specified in Test T7;
  (vi) a concentration of at least 0.04 g/l of ethanol is detected under the conditions specified in Test T8;
  and wherein the strain is produced by the method of the first to third aspects.

In one embodiment of the fourth to seventh aspects, the strain produces at least 0.2 grams of ethanol per liter within a period of 4 months under the conditions specified in Test T9.

In an eighth aspect, the invention provides an isolated *Saccharomyces* strain that is capable of growing at a rate of at least one generation per 48 hours using xylose as a sole carbon source for growth, wherein the capability of the strain to utilise xylose as a sole carbon source is obtained by non-recombinant methods.

The rate of growth of the strain may be any rate that is at least one generation per 48 hours. The rate of growth may be at least one generation per 36 hours. The rate of growth may be greater than one generation per 24 hours.

The rate of growth may be greater than one generation per 12 hours. The rate of growth may be greater than one generation per 10 hours. The rate of growth may be greater than one generation per 8 hours. The rate of growth may be greater than one generation per 6 hours. The rate of growth may be greater than one generation per 4 hours. The rate of growth may be greater than one generation per 2 hours. The rate of growth may be greater than one generation per 80 minutes.

In one embodiment, the strain is capable of growth using xylose as a sole carbon source at a rate that is substantially the same as the rate of growth of the strain using glucose as a sole carbon source for growth.

In one embodiment, the strain has a growth rate of at least one generation per 48 hours on xylose minimal mineral medium.

In one embodiment, the strain produces a 2-fold increase in biomass when grown under the conditions specified in Test T1. Typically, the strain produces at least a 5 fold increase in biomass when grown under the conditions specified in Test T1. Suitably, the strain produces at least a 10-fold increase in biomass when grown under the conditions specified in Test T1.

In one embodiment, the strain produces at least 0.01 g dry weight of biomass per 50 ml of culture when grown under the conditions specified in Test T2.

In various embodiments:(i) the strain expresses a non-recombinant enzyme having at least 1 unit of xylose reductase activity under the conditions specified in Test T4;
(ii) the strain expresses a non-recombinant enzyme having at least 1 unit of xylitol dehydrogenase activity under the conditions specified in test T5;
(iii) the strain expresses a non-recombinant enzyme having at least one unit of xylose reductase activity under the conditions specified in test T4, a non-recombinant enzyme having at least one unit of xylitol dehydrogenase activity under the conditions specified in test T5.

In a ninth aspect, the invention provides an isolated *Saccharomyces* strain which is capable of a growth rate of at least one generation per 48 hours using xylose as a sole carbon source for growth, and which is capable of expressing non-recombinant enzyme having an activity selected from the group consisting of xylose reductase and xylitol dehydrogenase, wherein the xylose reductase activity is at least 1 unit when determined by test T4, and the xylitol dehydrogenase activity is at least 1 unit when determined under the conditions specified in test T5.

The strain may be capable of expressing a non-recombinant enzyme having xylose reductase activity and a nonrecombinant enzyme having xylitol dehydrogenase activity. In one embodiment, the strain is capable of expressing a non-recombinant enzyme having xylulose kinase activity in addition to one or more non-recombinant enzymes having an activity selected from the group consisting of xylose reductase and xylitol dehydrogenase. Typically, the xylulose kinase activity is at least 5 units when determined by test T6.

Typically, the strain of the ninth aspect has a rate of growth of at least one generation per 48 hours using xylose as a sole carbon source.

In one embodiment, the strain produces at least a 2-fold increase in biomass when grown under the conditions specified in Test T1. Typically, the strain produces at least a 5-fold increase in biomass when grown under the conditions specified in Test T1. More typically, the strain produces at least a 5-fold increase in biomass when grown under the conditions specified in test T1.

The strain may produce at least 10 mg dry weight of biomass under the conditions specified in test T2. The strain may produce at least 30 mg dry weight of biomass under the conditions specified in test T2. The strain may produce at least 40 mg dry weight of biomass under the conditions specified in Test T2. Typically, the strain produces at least 50 mg dry weight of biomass under the conditions specified in test T2.

The strain may produce at least 0.01 g dry weight of biomass per 50 ml of culture when grown under the conditions specified in Test T2.

The *Saccharomyces* strain may further be capable of using xylitol as a sole carbon source for growth. Typically, the capability of the strain to utilise xylitol as a sole carbon source is obtained through non-recombinant methods.

In one embodiment, the strain produces at least a 5-fold increase in biomass when grown under the conditions specified in Test T7.

The *Saccharomyces* strain may be capable of aerobic or anaerobic growth using xylose as a sole carbon source. Typically, the growth is aerobic growth. However, the *Saccharomyces* strain may also grow anaerobically or microaerophilically using xylose as a sole carbon source.

The *Saccharomyces* strain may be capable of growth on glucose under anaerobic conditions.

The *Saccharomyces* strain may further be capable of utilising xylose to produce one or more of a carbon-based compound. Examples of suitable carbon-based compounds include alcohols, xylitol, organic acids such as acetic acid, glycerol, carbon dioxide, or other yeast components, metabolites and by-products including yeast extracts, proteins, peptides, amino acids, RNA, nucleotides, glucans, etc. Typically, the alcohol is ethanol.

The strain may produce ethanol when growing on xylose. The strain may use the xylose to produce ethanol without growing on the xylose. The strain may produce ethanol from xylose. Typically, the strain ferments xylose to produce ethanol.

The strain may produce ethanol at a concentration of at least 0.1 g/L under the conditions specified in Test T3.

The strain may produce ethanol at a concentration of at least 0.4 g/L under the conditions specified in Test T8.

The strain may produce at least 0.2 g of ethanol per liter within a period of 4 months under the conditions specified in Test T9.

The strain may produce at least 0.5 g of ethanol per L when inoculated at a cell density of at least $5 \times 10^8$ cells per ml into xylose-containing minimal mineral medium. The xylose-containing minimal mineral medium may contain glucose. Typically, the strain produces 0.5 g/L of ethanol within 5 hours of inoculation of the medium.

In one embodiment, the strain ferments xylose to produce at least 0.05 grams of ethanol per liter of culture under the conditions specified in Test T3.

The strain may be capable of utilising xylose as a sole carbon source to grow on solid medium, and/or in liquid medium. In one embodiment, the strain is capable of growth in liquid medium containing xylose as a sole carbon source. The liquid medium may be liquid mineral medium containing xylose as a sole carbon source.

The *Saccharomyces* strain may be a strain from any species of the genus *Saccharomyces*. Examples of suitable species of yeasts include *S. cerevisiae*, *S. paradoxus*, *S. mikatae*, *S. cariocanus*, *S. kudriavzevii*, *S. pastorianus* and *S. bayanus*. Typically the species is *Saccharomyces cerevisiae*. Typically the strain will be capable of mating with *Saccharomyces* of the same species. Typically the strain will be capable of mating with *Saccharomyces cerevisiae*. Typically, the strain is *Saccharomyces cerevisiae*.

In one embodiment of the eighth or ninth aspects, the *Saccharomyces* strain is recombinant.

In a tenth aspect, the invention provides an isolated non-recombinant *Saccharomyces* strain which produces an increase in biomass of at least 2-fold under the conditions specified in Test T1.

In one embodiment, the increase in biomass is at least 5-fold, typically at least 10-fold.

In a eleventh aspect, the invention provides an isolated non-recombinant *Saccharomyces* strain which has the following characteristics:
(a) Biomass of the strain increases at least 5-fold under the conditions specified in test T1;
(b) At least 10 mg dry weight of biomass is produced under the conditions specified in test T2.

In a twelfth aspect, the invention provides an isolated non-recombinant *Saccharomyces* strain which has the following characteristics:
(a) Biomass of the strain increases at least 10-fold under the conditions specified in test T1;
(b) At least 50 mg dry weight of biomass is produced under the conditions specified in test T2;
(c) A concentration of at least 0.1 g/L of ethanol is detected under the conditions specified in Test T3;
(d) at least 1 nanomole of NAD(P)H is reduced or oxidised per minute per mg of protein extract at 30° C. under the conditions specified in Test T4; and
(e) at least 1 nanomole of NAD(P)H is reduced or oxidised per minute per mg of protein extract at 30° C. under the conditions specified in Test T5.

In a thirteenth aspect, the invention provides an isolated non-recombinant *Saccharomyces* strain which has the following characteristics:
(a) Biomass of the strain increases at least 5-fold under the conditions specified in test T1;
(b) At least 40 mg dry weight of biomass is produced under the conditions specified in test T2;
(c) Biomass of the strain increases at least 5-fold under the conditions specified in Test T7;
(d) A concentration of at least 0.04 g/L of ethanol is detected under the conditions specified in test T8;
(e) at least 1 nanomole of NAD(P)H is reduced or oxidised per minute per mg of protein extract at 30° C. under the conditions specified in Test T4; and
(f) at least 1 nanomole of NAD(P)H is reduced or oxidised per minute per mg of protein extract at 30° C. under the conditions specified in Test T5.

Examples of suitable Saccharomyces strains that are capable of growth at a rate of at least one generation per 48 hours using xylose as a sole carbon source for growth are those that are deposited under the Budapest Treaty on the International Recognition of the Deposit of Microorganisms for the Purposes of Patent Procedure at the Australian Government Analytical Laboratories, 1 Suakin Street, Pymble, NSW 2073, Australia (now known as the National Measurement Institute (NMI), which is also an International Depository Institution under the Budapest Treaty, having the address: 1/153 Berne Street, Port Melbourne, VIC 3207), under deposit accession nos. NM04/41257, NM04/41258, NM05/45177 (ISO 10) and NM05/45178 (ISO 7). Deposit accession numbers NM04/41257 and NM04/41258 were deposited on 12 May 2004. Deposit accession numbers NM05/45177 and NM05/45178 were deposited on 16 May 2005. All restrictions imposed by the depositor on the availability to the public of the deposited material will be irrevocably removed upon the granting of a patent.

The *Saccharomyces* strain may be obtained by any method referred to herein in which the ability to utilise xylose as a sole carbon source for growth is obtained by non-recombinant methods. Methods that may be employed to obtain the strain include combinations of, natural selection, mating procedures, mutagenesis, or other so-called classical genetic methods known to those skilled in the art and discussed and referred to in, for example, Attfield and Bell (2003) "Genetics and classical genetic manipulations of industrial yeasts" in, Topics in Current Genetics, Vol 2. Functional Genetics of Industrial Yeasts (J. H. de Winde, ed.), Springer-Verlag Berlin Heidelberg or combinations thereof.

The ability to grow at a rate of at least one generation per 48 hours using xylose as a sole carbon source is typically obtained by mating between *Saccharomyces* strains and screening or selection for increased growth rate using xylose as a sole carbon source.

For example, the strain may be obtained by conducting rare or directed or mass matings between strains of sexually compatible *Saccharomyces*, followed by selection for strains that are capable of utilising xylose as a sole carbon source. The strain may be derived from one or more naturally occurring isolates of *Saccharomyces*, spontaneously mutated isolates, or it may be obtained by exposing one or more *Saccharomyces* strains to a mutagen and subsequently used in mating and selection strategies to screen or select for a mutant strain that is capable of utilising xylose as a sole carbon source. The obtained strain may be selected by any of the selection methods referred to herein.

In a fourteenth aspect, the invention provides a derivative of a strain of the fourth to thirteenth aspects.

Methods for the production of derivatives of yeast strains are well known in the art and include matings with other yeast strains, cell fusions, mutagenesis, and/or recombinant methods.

In a fifteenth aspect, the invention provides the use of a *Saccharomyces* strain of the fourth to fifteenth aspects, or a derivative of the fourteenth aspect, in production of yeast biomass. The yeast biomass may be used in, for example, the baking industry, for biomass products.

In a sixteenth aspect, the invention provides the use of a *Saccharomyces* strain of the fourth to thirteenth aspect, or a derivative of the fourteenth aspect, for the production of ethanol from xylose.

In a seventeenth aspect, the invention provides a method for the production of ethanol comprising incubating a *Saccharomyces* strain of the fourth to thirteenth aspects, or a derivative of the fourteenth aspect, with a xylose-containing medium, under conditions which permit the strain to ferment xylose to produce ethanol.

In an eighteenth aspect, the invention provides a method of converting xylose into yeast biomass, comprising culturing a *Saccharomyces* strain of the fourth to thirteenth aspects, or a derivative of the fourteenth aspect, with a xylose-containing medium under conditions which permit the strain to grow using the xylose as a carbon source for growth.

In a nineteenth aspect, the invention provides a method of producing yeast biomass comprising growing a *Saccharomyces* strain on or in a xylose-containing medium wherein at least a portion of the yeast biomass is produced using xylose as a carbon source for growth.

In a twentieth aspect, the invention provides a method of producing a compound from a *Saccharomyces* strain, comprising culturing the *Saccharomyces* strain on or in a xylose-containing medium under conditions which permit production of the compound, wherein the compound is produced by the strain using xylose as a carbon source.

In one embodiment, the compound is produced by the strain during growth using xylose as a carbon source.

In one embodiment, the method comprises the further step of recovering the compound.

The compound may be any compound that can be produced by the *Saccharomyces* strain. Examples of suitable compounds include ethanol, $CO_2$, enzymes, recombinant enzymes, recombinant proteins, yeast by-products, vitamins, nucleotides, ribonucleotides, deoxyribonucleotides, lipids, yeast proteins, xylitol.

It will be appreciated by those skilled in the art that growth of the yeast cells produces biomass, and therefore any method which results in growth will result in production of biomass. Thus, for example, production of ethanol from growth on xylose-containing medium will in addition produce biomass. In one embodiment, compounds are contained within the yeast cells in biomass and the compounds may be recovered from the yeast cells using methods well known in the art for extracting compounds from yeast cells.

In a twenty-first aspect, the invention provides a compound produced by the method of the eighteenth aspect.

BRIEF DESCRIPTION OF THE FIGURES

FIG. 1 shows a plot of the average doubling time of a population of *Saccharomyces cerevisiae* strains over time following application of the method of the invention.

DETAILED DESCRIPTION OF THE INVENTION

The practice of the present invention employs, unless otherwise indicated, conventional microbiology and classical genetics. Such techniques are known to the skilled worker, and are explained fully in the literature. See, for example, Sherman et al. "Methods in Yeast Genetics" (1981) Cold Spring Harbor Laboratory Manual, Cold Spring Harbor, N.Y.; European Patent number EP 0 511 108 B.

It is also to be understood that the terminology used herein is for the purpose of describing particular embodiments only, and is not intended to limit the scope of the present invention which will be limited only by the appended claims. It must be noted that as used herein and in the appended claims, the singular forms "a", "an", and "the" include plural reference unless the context clearly indicates otherwise. Thus, for example, a reference to "a cell" includes a plurality of such cells. Unless defined otherwise, all technical and scientific terms used herein have the same meaning as commonly understood by one of ordinary skill in the art to which this invention belongs. Although any materials and methods similar or equivalent to those described herein can be used to practice or test the present invention, preferred materials and methods are now described.

All publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Xylose is a sugar which is inexpensive, can be obtained from a renewable resource, and is available in large amounts. Xylose can represent a significant portion of hemicellulosic plant biomass. Plant biomass includes agricultural residues, paper wastes, wood chips and the like, and is renewable, and available at low cost in large amounts. Xylose is primarily present in hemicellulosic plant biomass as polymers known as xylan and hemicellulose. The polymers of xylose can be readily broken down into monomeric sugars either by chemical means such as acid hydrolysis, or by enzymatic means using enzymes such as xylanases. In paper manufacturing for example, xylose is one of the main sugars in the waste stream, where it contributes to biological oxygen demand (BOD) and thereby makes disposal of the waste-water environmentally difficult. For every kilogram of paper produced from hardwood, typically 100 grams of sugar is produced, 35 grams of which is xylose. Because of its abundance, xylose presents a major potential carbon source for producing yeast biomass and by-products of yeast metabolism such an ethanol.

In one aspect there is provided to a *Saccharomyces* strain that is capable of growing at a rate of at least one generation per 48 hours using xylose as a sole carbon source. The inventors have found that it is possible to obtain strains of *Saccharomyces* that are capable of relatively rapid growth using xylose as a sole carbon source without the need to use recombinant DNA technology. This is an unexpected result as it was previously believed that strains of *Saccharomyces* were not capable of growth on xylose as a sole carbon source. Until the present invention, *Saccharomyces* strains capable of growth at rates of at least one generation per 48 hours using xylose as a sole carbon source have only be obtained by introducing into *Saccharomyces* strains cloned xylose utilisation genes from other organisms that are capable of growth on xylose. Alternatively unnaturally occurring combinations of cloned *Saccharomyces* gene promoters and cloned *Saccharomyces* DNA sequences have been generated using recombinant methods and introduced into *Saccharomyces* strains. Thus, prior to the present invention, obtaining strains of *Saccharomyces* capable of utilising xylose as a sole carbon source has not been possible unless either xylose utilisation genes from other organisms that are capable of growth on xylose have been cloned and introduced into the *Saccharomyces* strain, or strong *Saccharomyces* gene promoters have been operably linked to other *Saccharomyces* DNA sequences and introduced into the *Saccharomyces* strain using recombinant DNA methods.

Prior to the present invention, no non-recombinant yeast from the genus *Saccharomyces* were capable of a growth rate of at least one generation per 48 hours using xylose as a sole carbon source. U.S. Pat. No. 4,511,656 discloses yeast strain ATCC No. 20618 which is a non-recombinant yeast mutant that is capable of producing ethanol when incubated in medium containing xylose. However, ATCC 20618 is not from the genus *Saccharomyces*. The morphology of the colonies produced by ATCC No. 20618 is not consistent with those produced by *Saccharomyces*. ATCC No. 20618 does not sporulate, does not mate with standard strains of *Saccharomyces cerevisiae*, and sequencing of the ITS regions and histone H3-H4 intergenic region of ATCC No 20618 reveals that it is not of the genus *Saccharomyces*, but is closely related to *Candida tropicalis*.

Accordingly, ATCC 20618 is phylogenetically distant from *Saccharomyces* as defined by Kurtzman (2003) FEMS Yeast Research 4:233-245 and as defined herein. *Candida tropicalis* is well known to utilise xylose. Additionally, the mutants disclosed in U.S. Pat. No. 4,511,656 were only demonstrated to produce ethanol when provided with growth nutrients such as yeast extract, malt extract and peptone in the growth medium. These growth nutrients provide alternative fermentable carbon sources to xylose. Thus, U.S. Pat. No. 4,511,656 does not disclose strains of *Saccharomyces* that are capable of growth on, or fermentation of, xylose as a sole carbon source.

Furthermore U.S. Pat. No. 4,511,656 teaches that yeast capable of producing ethanol are selected which form colonies on xylose but not xylitol. Without wishing to be bound by theory, the inventors believe that contrary to the teaching of U.S. Pat. No. 4,511,656, the metabolism of xylitol, which is an intermediate in xylose utilisation, might be expected to be advantageous to growth on xylose and ethanol production from xylose.

The inventors have found contrary to the teaching of the prior art, that not only are *Saccharomyces* strains capable of very slow growth on xylose as a sole carbon source, but that the growth rate using xylose as a sole carbon source of *Saccharomyces* strains can be increased without introducing cloned xylose utilisation genes.

In one aspect, there is provided an isolated *Saccharomyces* strain which is capable of growing at a rate of at least one generation per 48 hours using xylose as a sole carbon source. As used herein, a *Saccharomyces* strain is a strain of the genus *Saccharomyces* as defined in Kurtzman (2003) FEMS Yeast Research vol. 4 pp. 233-245.

As used herein, the expression "capable of growing at a rate of at least one generation per 48 hours using xylose as a sole carbon source for growth" means that the strain is capable of using xylose as the only source of carbon for generation of energy, and synthesis of molecules that are necessary for growth of the strain, to attain a growth rate of at least one generation per 48 hours. The term "one generation" will be clear to those skilled in the art to mean one cycle of cell division. The strain will preferably be capable of growth in solid and liquid media in which xylose is the only carbon source. It will be appreciated by persons skilled in the art that a strain that is capable of growing at a rate of at least one generation per 48 hours using xylose as a sole carbon source will be capable of growth on solid and/or in liquid minimal mineral media, in which xylose is the sole carbon source. An example of a suitable liquid medium is the commercially available DIFCO Laboratories Yeast Nitrogen Base without amino acids, which contains all essential inorganic salts and vitamins necessary for cultivation of yeasts except a source of carbohydrate or amino acids, supplemented with between 0.01% and 50% xylose, typically 1% and 10% xylose, suitably 5% xylose. Typically, solid medium is liquid medium that has been solidified by the addition of a gelling agent such as agar. It will also be appreciated by persons skilled in the art that a strain that is capable of growth using xylose as a sole carbon source may also be capable of growth on many other sugars.

The capability of the strain to utilise xylose as a sole carbon source is obtained by non-recombinant methods. As used herein, the expression "non-recombinant methods" refer to any methods that do not utilise recombinant DNA technology to produce in the *Saccharomyces* strain the ability to utilise xylose. In other words, the genes that confer on the strain the ability to utilise xylose for growth have not been introduced into the strain using recombinant methods. As used herein, a "recombinant method" is a method in which one or more genes are introduced into an organism using recombinant DNA techniques. As used herein, recombinant DNA techniques refer to techniques in which genetic information is manipulated in vitro, such as when genes are isolated and cloned from an organism. Thus, non-recombinant methods are methods which do not involve the manipulation of genetic information in vitro. A non-recombinant strain is a strain into which recombinant nucleic acid has not been introduced.

Non-recombinant methods may include, for example, mutagenesis, classical mating, cytoduction, cell fusion such as protoplast fusion, and combinations thereof. The non-recombinant method may comprise culturing a population of genetically diverse yeast cells of Saccharomyces under conditions which permit combining of the DNA between yeast cells in vivo, and screening or selecting for yeast cells having an increased growth rate using xylose as a sole carbon source, typically by incubating a genetically diverse population of yeast cells in or on xylose-containing medium for sufficient time to select yeast cells having an increased growth rate using xylose as a sole carbon source.

It will be understood by those skilled in the art that the genetic information which confers the ability of the Saccharomyces strain to grow at a rate of at least one generation per 48 hours utilising xylose as a sole carbon source is obtained from the genus Saccharomyces. In other words, all the genetic information necessary for growth at a rate of at least one generation per 48 hours is obtained from within the gene pool of the genus Saccharomyces. Typically, the genetic information which confers the ability of the Saccharomyces strain to grow at a rate of at least one generation per 48 hours utilising xylose as a sole carbon source for growth is obtained from a genetically diverse population of non-recombinant Saccharomyces strains. As discussed above, prior to the present invention, the gene pool of the genus Saccharomyces was thought not to contain the genetic information for conferring the ability to utilise xylose as a sole carbon source for growth.

In another aspect, there is provided isolated Saccharomyces strains which have the ability to grow on xylose as a sole carbon source at a growth rate of at least one generation per 48 hours, and which are capable of expressing non-recombinant enzyme having an activity selected from the group consisting of xylose reductase and xylitol dehydrogenase. The enzyme has an activity of at least unit as determined by Test T4 for xylose reductase, and Test T5 for xylitol dehydrogenase. Tests T4 and T5 are defined herein. In one embodiment, the xylose reductase activity is at least 1.5 units, suitably at least 3 units. In one embodiment, the xylitol dehydrogenase activity is at least 5 units, suitably at least 8 units.

There is also provided a method for producing a Saccharomyces strain that is capable of growth at a desired growth rate using xylose as a sole carbon source. The "desired growth rate" may be any growth rate which is greater than the growth rate of the yeast cells of Saccharomyces prior to applying the method of the invention. The desired growth rate will be greater than the growth rate of Saccharomyces cerevisiae strain NL67 on xylose as a sole carbon source. The desired growth rate may be at least one generation per 48 hours, suitably greater than one generation per 24 hours, suitably greater than one generation per 12 hours, typically greater than one generation per 10 hours, more typically greater than one generation per 8 hours, and may be as high as the rate of growth of Saccharomyces on glucose, which is about one generation per 80 minutes.

The method comprises providing a population of genetically diverse non-recombinant yeast cells of Saccharomyces. As used herein, the expression "genetically diverse non-recombinant yeast cells" refers to at least two non-recombinant yeast cells that have distinct genotypes. The genetically diverse non-recombinant yeast cells may be a mixture of yeast cells of different Saccharomyces strains obtained from the wild, from wine, distilling and beer fermentation, from baking applications, or from any other source of Saccharomyces. The genetically diverse population of non-recombinant yeast cells of Saccharomyces may be derived from a single strain that is sporulated to derive genetically diverse progeny. The genetically diverse population of non-recombinant yeast cells of Saccharomyces may include one or more yeast cells of Saccharomyces strains that have been exposed to a physical or chemical mutagen such as, for example, ultraviolet light, X-ray or Gamma ray, or ethylmethanesulphonate, nitrosoguanidine, mitomycin C, bleomycin, or any other agents that cause alterations to DNA base sequences. Thus, genetically diverse non-recombinant yeast cells includes within its scope yeast cells of strains that have been generated by mutagenesis. Methods for mutagenesis of yeast, and in particular, mutagenesis of Saccharomyces cerevisiae, are known to persons skilled in the art and are described in, for example, Sherman et al. "Methods in Yeast Genetics" (1981) Cold Spring Harbor Laboratory Manual, Cold Spring Harbor, N.Y. The genetically diverse population of non-recombinant yeast cells of Saccharomyces may also include yeast cells with spontaneously occurring mutations. The population of genetically diverse non-recombinant yeast cells of Saccharomyces may be all the same species, or may be different species of Saccharomyces. Typically, the different species are capable of mating between each other. For example, the population of genetically diverse non-recombinant yeast cells may comprise different strains of Saccharomyces cerevisiae, or any other Saccharomyces species, obtained from any of the sources mentioned above. Examples of suitable Saccharomyces species include S. cerevisiae, S. paradoxus, S. mikatae, S. cariocanus, S. kudriavzevii, S. pastorianus and S. bayanus. Typically, the population of genetically diverse yeast cells of Saccharomyces are the same species. Typically, the species is Saccharomyces cerevisiae.

Examples of yeasts that could be used to provide starting inocula for populations of genetically diverse non-recombinant yeast cells include Saccharomyces strains available from well known culture collections such as American Type Culture Collection (ATCC), e.g. ATCC 4111, ATCC 26603, ATCC 38559, the National Collection of Yeast Cultures (NCYC) e.g. S. cerevisiae NCYC 995, NCYC 996, the Central Bureau voor Schimmel Cultures (CRBS) e.g. S. cerevisiae CBS 745.95, CBS 755.95, or isolated from commercially available yeasts sold by any number of companies for use in traditional formulations such as baking, brewing, wine, distilling, etc.

The population of genetically diverse non-recombinant yeast cells of Saccharomyces are cultured under conditions which permit combining of DNA between the yeast cells. Combining of DNA between the yeast cells may be by any method suitable for combining DNA from at least two yeast cells, provided the method is not a recombinant method. Examples of suitable methods for combining the DNA of yeast cells include mating and cytoduction. As used herein, the term "mating" refers to the process of exchange and recombination of DNA between at least two yeast cells, including by classical genetic mating methods, directed mating, mass mating, rare mating, cell fusion, etc. For example, classical genetic crosses or cell fusion may be used to generate intraspecific or interspecific hybrids.

In one embodiment, the yeast cells are cultured under conditions which permit mating between the yeast cells. Typically, the yeast cells are cultured under conditions which permit mating by sporulating the yeast cells and thereafter mating the sporulated yeast. For example, the yeast cells may be mated by:
(a) sporulating the yeast cells;
(b) germinating the sporulated yeast cells;
(c) hybridising compatible mating types of the sporulated yeast cells.

Typically, the yeast cells are mated by:
(a) pooling the population of genetically diverse non-recombinant yeast cells;
(b) sporulating the pooled cells and germinating the spores to produce haploid cells;
(c) hybridisation of compatible mating types of the haploid cells to produce hybrid yeast cells.

Methods for sporulation, obtaining haploids and hybridisation of the haploids to produce hybrid yeast cells are known in the art and are described in, for example, Chapter 7, "Sporulation and Hybridisation of Yeast" by R. R. Fowell, in "The Yeasts" vol 1 edited by A. H. Rose and J. S. Harrison, 1969, Academic Press; EP 0 511 108 B. Typically, the mating is mass mating. Mass mating involves culturing at least two and typically millions of different yeast cells together in a manner which permits mating to occur between compatible mating types. Methods for mass mating are described in, for example, Higgins et al. (2001), Applied and Environmental Microbiology vol. 67, pp. 4346-4348; Lindegren (1943), Journal of Bacteriology vol. 46 pp. 405-419.

In another embodiment, the yeast are cultured under conditions which permit cell fusion. Methods for the generation of intraspecific or interspecific hybrids using cell fusion techniques are described in, for example, Morgan (1983) Experientia suppl. 46: 155-166; Spencer et al. (1990) in, Yeast Technology, Spencer J F T and Spencer D M (eds.), Springer Verlag New York. Cytoduction methods are described in, for example, Inge-Vechtomov et al. (1986) Genetika 22: 2625-2636; Johnston (1990) in, Yeast Technology, Spencer J F T and Spencer D M (Eds.), Springer Verlag New York; Polaina et al. (1993) Current Genetics 24: 369-372.

The yeast cells are screened or selected for yeast cells which have an increased growth rate using xylose as a sole carbon source for growth. The yeast cells are screened or selected to enrich or identify yeast cells which have an increased rate of growth using xylose as a sole carbon source. The yeast cells are screened or selected typically by incubating the yeast cells on or in a xylose-containing medium. The yeast cells are screened or selected for those yeast cells that have an improved ability to grow using xylose as a sole carbon source for growth. The improved ability will typically be an increase in growth rate using xylose as a sole carbon source towards the desired growth rate. An increase in growth rate is an increase in the growth rate of a yeast cell relative to the growth rate of cells prior to culturing the yeast cells under conditions which permit combining of DNA between yeast cells. In one embodiment, the yeast cells are selected. The terms "selected" or "selecting" refers to a process in which the yeast cells that have an improved ability to grow using xylose as a sole carbon source for growth at the desired growth rate become enriched in the population. The yeast cells may be selected by incubating the yeast cells on or in xylose-containing medium for sufficient time to permit yeast cells capable of growth on xylose as a sole carbon source to grow using xylose as the carbon source, and thereafter collecting the yeast cells that grow. The inventors have found that by incubating the yeast cells for sufficient time to allow even slow growing yeast to grow using xylose as a carbon source, and thereafter collecting the yeast cells that grow, including the slow growing yeast cells, the faster growing yeast cells will represent a greater proportion of the collected yeast cells and therefore be enriched in the collected yeast cells, but genetic diversity of the yeast cell population is substantially maintained by also including slow growing yeast cells. For example, by plating mated yeast cells on solid minimal media containing xylose as a sole carbon source, cells capable of more rapidly utilising xylose as a sole carbon source would generate larger colonies, and as a consequence, those cells would be selected for and the desired genotype(s) enriched in the population. However, by also collecting the smaller colonies, the genetic diversity of the population would be substantially maintained for the next repeat of steps (b) and (c). Thus, by incubating the yeast cells on xylose-containing medium for sufficient time to permit the yeast cells to grow using xylose as a carbon source, it is possible to not only select for those yeast cells with increased growth rate on xylose, but to also maintain the genetic diversity of the population for repeated cycles of steps (b) and (c). Enhanced selection may be applied by reducing the time the yeast cells are incubated on the xylose-containing medium such that only yeast cells which grow using the xylose as a carbon source within a preselected time period are selected. Yeast cells of this type may be selected by incubating the yeast cells on or in the xylose-containing medium for sufficient time to permit yeast cells having an increased growth rate using xylose as a sole carbon source to grow using xylose as the carbon source, and thereafter collecting the yeast cells that grow. Using this approach, greater selective pressure is placed on the yeast cells to grow at an increased rate, but as there is likely to be insufficient time for a portion of the slow growing yeast cells to grow, some genetic diversity may be lost for further repeats of steps (b) and (c).

In another embodiment, the yeast cells are screened. As used herein, the terms "screened" or "screening" refers to a process in which the yeast cells that have an improved ability to grow using xylose as a sole carbon source for growth at the desired growth rate are first identified, and subsequently isolated. The yeast cells may be screened by incubating the yeast cells on or in xylose-containing medium for sufficient time to permit yeast cells having an increased growth rate using xylose as a sole carbon source to grow using xylose as the carbon source, and thereafter collecting the yeast cells that grow fastest using the xylose as a carbon source. For example, yeast cells that have an improved ability to grow using xylose as a sole carbon source may be identified on rich xylose-containing medium as those cells that grow faster and therefore form larger colonies than the yeast cells do not have an improved ability to grow using xylose as a sole carbon source. The larger colonies that appear on the plate can therefore be isolated in preference to the smaller colonies to thereby isolate yeast cells that have an improved ability to grow using xylose as a sole carbon source for growth at a desired growth rate.

As discussed above, the yeast cells are screened or selected typically by incubating the yeast cells on or in a xylose-containing medium. A "xylose-containing medium" may be any medium which contains xylose and provides a selective advantage to those yeast cells which have an ability to grow using xylose as a sole carbon source more efficiently or faster than other strains. As used herein, a "selective advantage" is the ability of a cell or strain to undergo a greater number of cell divisions than other cells or strains because of some attribute, in this case, the ability to grow efficiently using xylose. Thus, a medium that provides a selective advantage to a strain will permit that strain to grow faster in that medium compared to other strains to which the medium does not provide a selective advantage. It will be appreciated by those skilled in the art that yeast can be grown on a wide range of media that include at least one source of carbon, a source of nitrogen, a source of phosphorus, a source of sulphate, trace elements and vitamins. The xylose-containing medium may be a minimal media or a complex media. In one embodiment, the xylose containing medium is a minimal medium. A suitable minimal medium may comprise, for example, DIFCO Yeast Nitrogen Base Formulae (see Difco manual "Dehydrated culture media and reagents for microbiology" $10^{th}$ Edition, Difco Labs 1984), together with xylose at a concentration of between 0.1% and 50%, typically 2% and 15%, more typically 5%. In another embodiment, the xylose-containing medium may be a complex medium. The concentration of xylose in the complex medium may be between 0.1% and 50%, typically between 2% and 30%, more typically between 2% and 15%. In one embodiment, the complex medium is complete rich media. An example of complete rich medium is medium which comprises yeast extract at between 0.5 and 2%, preferably 0.5%, peptone at between 0.5% and 2%, preferably 1%, and xylose at a concentration of between 0.5% and 50%, typically 2% and 15%, more typically 5%. In another embodiment, the complex medium is selected from the group consisting of molasses, starch hydrolysates, cellulosic or hemicellulosic biomass hydrolysate (such as bagasse, stover, wood pulp, straw, waste paper, etc), and combinations thereof, optionally supplemented with xylose, and/or nutrients. It will be appreciated by persons skilled in the art that solid medium may be any of the abovementioned media typically supplemented with between 1% and 10% agar, more typically between 1% and 5% agar, still more typically between 1% and 2% agar.

The yeast cells may be screened or selected by incubating the cells on solid and/or liquid medium. In one embodiment, the yeast cells are screened or selected by incubating the cells on solid medium. In another embodiment, the yeast cells are screened or selected by incubating the yeast cells in liquid medium. In a preferred embodiment, the yeast cells are screened or selected by incubating the yeast cells first on solid medium, and subsequently on liquid medium. For example, the method may comprise:
(a) providing a population of genetically diverse non-recombinant yeast cells of Saccharomyces;
(b) culturing the yeast cells under conditions to permit mating of the yeast cells;
(c) screening or selecting the yeast cells by incubating the yeast cells on a solid xylose-containing medium;
(d) repeating steps (b) and (c) with the screened or selected cells forming the population of genetically diverse non-recombinant yeast cells of Saccharomyces, until one or more yeast cells have acquired the ability to grow at the desired growth rate using xylose as a sole carbon source for growth.

Typically, steps (b) and (c) are repeated until one or more yeast cells have acquired a growth rate on xylose that is sufficient to permit the cells to be conveniently grown in liquid medium containing xylose as a sole carbon source. For example, the growth rate on solid minimal mineral medium containing 2% to 5% w/v xylose at which a strain may be transferred to growth in liquid minimal mineral medium containing 2% to 5% w/v xylose as a sole carbon source will typically be reached following at least 2 repeats of steps (b) and (c). More typically at least 5 repeats of steps (b) and (c). Even more typically, at least 10 repeats of steps (b) and (c). It will be appreciated by those of skill in the art that the time at which the yeast cells may be selected or screened by incubating in liquid medium will vary depending on the population and can readily be determined by incubating a small portion of the population in liquid medium at each repeat of steps (b) and (c). Thereafter, the method may comprise:
(a) providing a population of genetically diverse non-recombinant yeast cells of Saccharomyces;
(b) culturing the yeast cells under conditions to permit mating of the yeast cells;
(c) screening or selecting the yeast cells by incubating the yeast cells in liquid xylose-containing medium;
(d) repeating steps (b) and (c) with the screened or selected cells forming the population of genetically diverse non-recombinant yeast cells of Saccharomyces, until one or more yeast cells have acquired the ability to grow at the desired growth rate using xylose as a sole carbon source for growth.

The yeast cells are typically incubated on or in the xylose-containing medium for sufficient time to allow the yeast cells capable of growth using xylose as a sole carbon source to grow. As discussed above, the length of time will at least be a sufficient length of time to allow the yeast cells that have an increased rate of growth using xylose as a sole carbon source to grow. Typically, the length of time will be a sufficient length of time to permit growth of yeast cells that do not have an increased rate of growth using xylose as a sole carbon source. In other words, the length of time will be sufficient to permit substantially all the yeast cells to grow on the xylose. The length of time may vary depending on the population of genetically diverse non-recombinant yeast cells, and will also vary depending on the types of medium used and how many cycles or repeats of steps (b) and (c) have been conducted. As each cycle is repeated, it is envisaged that the time will become less as the method screens or selects for populations that grow faster using xylose with each repeat of steps (b) and (c), independent of whether solid or liquid medium is used. It will also be appreciated by persons skilled in the art that even in complex medium containing sugars other than xylose, it is envisaged that some or all of the sugars other than xylose will eventually be depleted through growth, and that the presence of xylose will therefore eventually confer a selective advantage to those strains that grow faster on xylose as a sole carbon source.

The yeast cells may be incubated in liquid xylose-containing medium for a sufficient amount of time to permit the yeast cells that are most efficient at growing on xylose as a sole carbon source to outgrow those yeast cells that are less efficient at growing on xylose. Typically the amount of time is sufficient to permit growth of even those yeast cells that do not have an increased growth rate using xylose as a sole carbon source. As discussed above, faster growing cells will be greater in numbers and therefore selected from. Thus, the use of liquid xylose-containing medium provides a convenient way to select for those yeast cells that are capable of utilising xylose at a faster rate than the rest of the yeast cell population. The period of growth in liquid xylose-containing medium is typically reduced with each cycle as the screened or selected yeast cells become more efficient at utilising xylose. Following screening or selecting of the yeast cells by culturing the cells in liquid xylose-containing medium, the cells are typically harvested from the liquid medium and mated without further separation or isolation of the cells. Thus, the screened or selected yeast cells are typically mated as a pool. The mating methods are the same as those following screening and selection on solid xylose-containing medium.

It will be appreciated that the yeast cells may be incubated in or on xylose-containing medium under any conditions which select or screen for xylose-utilising yeast strains in populations. By way of example, populations could be cultured:

(a) in or on xylose minimal medium under aerobic, microaerophilic, anaerobic conditions;
(b) in or on xylose rich medium under aerobic conditions, microaerophilic, anaerobic conditions.

The above medium may include other carbon sources (eg. sugars such as glucose, galactose, polyols such as xylitol, glycerol, organic acids and their salts such as acetic acid and acetates etc.) in addition to xylose. For example, the yeast cells may be exposed to stresses such as sub- or supra-optimal pH, hyper- or hypo-osmotic pressure, ionic stresses from salts, alcohol stress from addition of ethanol or other alcohols, stress from other organic inhibitors such as furfurals and their derivatives, sub- or supra-optimal temperatures, presence, of absence of xylose and then subsequently selected or screened for their ability to recover from the stresses whilst utilising xylose as the sole carbon source. It is anticipated that combinations of different selective conditions could be applied to the populations.

It will be appreciated that step (c) may be repeated any number of times before isolating the yeast cells or repeating step (b). For example, populations selected in liquid xylose-containing medium may be continually subcultured into fresh medium to further screen or select for yeast cells having the desired growth rate.

It will also be appreciated by those skilled in the art that steps (b) and (c) may be repeated any number of times to screen or select for non-recombinant yeast cells in which the rate of growth on xylose as a sole carbon source is progressively increased with each repeated cycle. This process is thus repeated for as many times as is required in order to obtain a strain that exhibits the desired growth rate using xylose as a sole carbon source.

Thereafter, the method typically comprises the step of isolating one or more yeast cells which have the desired growth rate. It will be appreciated by persons skilled in the art that the method typically generates a population of genetically diverse non-recombinant yeast cells of *Saccharomyces* which have the desired growth rate. Accordingly, in one embodiment, the method may be used to produce a population of *Saccharomyces* strains which are capable of growth utilising xylose as a sole carbon source at a desired growth rate. The population may be isolated without separating individual strains. This may be achieved, for example, by simply pooling the population of *Saccharomyces* strains that are produced by the method.

In another embodiment, individual strains of *Saccharomyces* which are capable of growth utilising xylose as a sole carbon source may be isolated. This may be achieved using standard microbiological techniques such as providing suitable colonies, streaking the yeast on agar plates for single colony isolates, or any other methods for isolation of pure cultures. Such methods are described in Cruickshank et al. (1975) "Medical Microbiology", 12$^{th}$ edition, volume two: The practice of medical microbiology, published by Churchill Livingstone.

Also provided is a method of generating a derivative of a *Saccharomyces* strain with increased growth rate on xylose as a sole carbon source for growth. The *Saccharomyces* strain from which the derivative is generated typically has a desired property. The method comprises step (a) of providing the strain as part of a population of genetically diverse non-recombinant yeast cells of *Saccharomyces*. In other words, yeast cells of the strain make up a portion of the population. The yeast cells of the genetically diverse population may be from any of the sources mentioned above. In step (b), the yeast cells of the population of genetically diverse yeast cells are cultured under any of the conditions mentioned above which permit mating of the yeast cells of the population. In step (c), the yeast cells are screened or selected for derivatives which have an increased growth rate. The increased growth rate is an increase in growth rate of the derivative relative to the growth rate of the strain. Typically, the yeast cells are screened or selected by incubating the yeast cell in or on xylose containing medium as mentioned above. The xylose-containing medium may in addition contain factors which select or screen for the derivative strain. For example, the strain may comprise selectable markers such as antibiotic resistance markers or other types of markers which permit derivatives of the strain to be distinguished from other yeast cells of the population of genetically diverse yeast cells. This allows simultaneous screening or selection for yeast cells having increased growth using xylose as a sole carbon source, and carrying the selectable marker. This permits distinguishing the derivatives from the rest of the genetically diverse population. Suitable selectable markers include, for example, ADE2, HIS3, LEU2, URA3, LYS2, MET15, TRP1, URA4, sulfite resistance or p-fluoro-DL-phenylalanine resistance (Cebollero and Gonzalez (2004) Applied and Environmental Microbiology, Vol 70: 7018-7028). Methods for screening and selecting for growth using xylose are as mentioned above. Steps (b) and (c) may be repeated any number of times until a derivative is obtained with an increase in growth rate. Once the growth rate has been increased, the derivative is isolated. Methods for isolated are as mentioned above.

Also included within the scope of the present invention are *Saccharomyces* strains produced by the method of the invention. The *Saccharomyces* strain may be any species of *Saccharomyces* as defined phylogenetically by Kurtzman (2003) FEMS Yeast Research 3:417-432, and include *S. cerevisiae, S. paradoxus, S. mikatae, S. cariocanus, S. kudriavzevii, S. pastorianus* and *S. bayanus*. Methods for mating between strains of *Saccharomyces cerevisiae* and non-cerevisiae strains are discussed in, for example, Johnston J R and Oberman H (1979) Yeast Genetics in Industry, in Bull M J (ed.) Progress in Industrial Microbiology, Elsevier, Amsterdam vol 15, pp. 151-205; Pretorius I S (2000) Tailoring wine yeast for the new millenium: novel approaches to the ancient art of wine making. Yeast 16: 675-729; P. V. Attfield and P. J. L. Bell (2003) Genetics and classical genetic manipulations of industrial yeasts, in Topics in Current Genetics Vol. 2, J. H. de Winde (ed) Functional Genetics of Industrial Yeasts, Springer-Verlag Berlin Heidelberg.

It will be appreciated by persons skilled in the art that once a strain of *Saccharomyces* is obtained that is capable of utilising xylose as a sole carbon source for growth at a desired growth rate, strains may be derived from that strain using methods known in the art for strain production including for example, classical genetic crossing methods, mutagenesis methods, recombinant methods, or any other methods for generating strains of *Saccharomyces*.

The strain capable of a growth rate of at least one generation per 48 hours utilising xylose as a sole carbon source may be mated with other strains of *Saccharomyces*, preferably with other strains of *Saccharomyces cerevisiae*. For example, it is envisaged that the above methods may produce multiple strains of *Saccharomyces* that are capable of a growth rate of at least one generation per 48 hours utilising xylose as a sole carbon source for growth. Thus, a first strain capable of a growth rate of at least one generation per 48 hours utilising xylose as a sole carbon source for growth may be mated with a second strain capable of a growth rate of at least one generation per 48 hours utilising xylose as a sole carbon source for growth. Matings of this type may be performed, for example, to obtain a strain of Saccharomyces with even further enhanced or improved ability to utilise xylose as a sole carbon source. For example, it is envisaged that different strains of Saccharomyces that are capable of rapid growth utilising xylose as a sole carbon source may be mated to obtain mated strains that are capable of faster growth on xylose, or that are more efficient at producing products such as ethanol or carbon dioxide when using xylose as a carbon source.

Strains of Saccharomyces that are capable of growth rates of at least one generation per 48 hours using xylose as a sole carbon source may be mated with strains of Saccharomyces that are less capable of utilising xylose as a sole carbon source. Matings of this type may be performed, for example, to transfer the improved ability to utilise xylose as a sole carbon source to a Saccharomyces strain that has one or more desirable properties not found in the strain that has an improved ability to utilise xylose as a sole carbon source. For example, a Saccharomyces cerevisiae strain less capable of using xylose as a sole carbon source for growth may have desirable characteristics for the baking industry, and it may be advantageous to mate this strain with a strain that is capable of growth at a rate of at least one generation per 48 hours utilising xylose as a sole carbon source in order to develop a baker's yeast that can be grown more rapidly or efficiently on xylose and used subsequently in baking applications. Similarly, yeasts that can be used for other industrial purposes such as distilling, wine making, yeast extracts, enzymes, heterologous proteins, or any other purposes may be mated with strains which have an improved ability to use xylose as a sole carbon source in order to enable production of biomasses or yeast by-products on xylose media.

By mating a Saccharomyces strain, for example, a Saccharomyces cerevisiae strain, in which the capability to grow at a rate of at least one generation per 48 hours utilising xylose as a sole carbon source is obtained by non-recombinant methods with a recombinant strain in which one or more genes for xylose utilisation have been introduced by recombinant methods, it is envisaged that strains with even further improvements in xylose utilisation can be produced. It will be appreciated by those skilled in the art that the genes for xylose utilisation that have been introduced recombinantly would simply supplement those genes already present in the strain through non-recombinant methods.

It will also be appreciated by persons skilled in the art that while the ability to utilise xylose is obtained by non-recombinant methods, recombinant DNA technology may be used to supplement the capability of the strain to utilise xylose as a sole carbon source. For example, one or more xylose utilisation genes from other sources may be introduced into the strain to supplement xylose utilisation. For example, xylose isomerase from Piromyces sp. may be integrated into the genome as described in Kuyper et al. merely to supplement xylose utilisation. Xylose reductase (XYL 1), or xylitol dehydrogenase (XYL2) from Pichia stipitis may be cloned into Saccharomyces as described in Wahlbom et al. (2003) to supplement the capability of the strain to utilise xylose. However, it will be understood by persons skilled in the art that the addition of sequences for utilisation of xylose by recombinant methods is merely to supplement the strains existing capability of a growth rate of at least one generation per 48 hours utilising xylose as a sole carbon source.

In a further example, one or more genes that encode for metabolic activities that might impinge on efficiency of xylose utilisation by Saccharomyces other than through direct actions on xylose, xylitol or xylulose, could be introduced into the non-recombinant strains and their expression modified using recombinant DNA techniques. In some cases it might be desirable to increase the expression of certain genes whereas in other cases it might be desirable to reduce or eliminate expression of certain genes. Target genes for altered expression could include those encoding cytoplasmic, mitochondrial or other organelle metabolic activities. Such genes could encode for activities involved in sugar transport, nutrients transport, glycolysis, terminal steps of fermentation, pentose phosphate pathway, gluconeogenesis, tricarboxylic, acid pathway, glyoxylate cycle, electron transport chain, intracellular redox balance, interaction between fermentation and respiration, amino acid synthesis and metabolism etc. Examples of genes that might be modified by recombinant DNA technologies include RPE1, RK11, TAL1, and TKL1 or any other genes that might improve the ability of yeasts to use xylose as a sole carbon source.

It will be further appreciated by a person skilled in the art that one or more genes for xylose utilisation may be introduced into the strain using recombinant methods. Methods for the production of recombinant yeast are well known in the art and are described in for example, Guthrie and Fink (1991) "Guide to Yeast Genetics and Molecular Biology", Methods in Enzymology Vol 194, Academic Press. Genes or sequences of interest may be cloned into suitable vectors for transformation into the yeast cell. The gene or sequence of interest is cloned into a suitable expression vector such as pMA91 Dobson et al. (1984) EMBO Journal 3: 1115), which comprises the appropriate regulatory regions for expression in the yeast strain. Other vectors include episomal, centromeric, integrative, modified expression vectors known to those skilled in the art (see for example, Guthrie and Fink (1991) "Guide to Yeast Genetics and Molecular Biology", Methods in Enzymology Vol 194, Academic Press). Regulatory regions that may be suitable for expression in yeast may include, for example, MAL, PGK1, ADH1, GAL1, GAL10, CUP1, GAP, CYC1, PHO5. Alternatively, the regulatory regions of the gene itself may be used to express the gene in Saccharomyces. The gene or sequence of interest may be integrated into the yeast genome, such as into the ribosomal RNA locus, for instance. For this purpose, the ribosomal sequences of a suitable vector (eg. plasmid pIRL9) are released, and cloned appropriately to a BS+ vector. The gene or sequence of interest is operably linked to suitable yeast promoter and terminator regions to form an expression cassette, and the expression cassette is subsequently cloned into the cloned ribosomal sequences. From this resulting plasmid the expression cassette, flanked by ribosomal sequences can be released as a single fragment using appropriate restriction enzymes. The released fragment can be cotransformed with an autonomously replicating plasmid carrying a suitable marker for transformation into a yeast using methods known in the art (see for example Guthrie and Fink (1991) "Guide to Yeast Genetics and Molecular Biology", Methods in Enzymology Vol 194, Academic Press). The plasmid can be later removed from the cell by cultivating the cells in conditions that do not select for the plasmid.

The Saccharomyces spp. strain of the present invention may be used for any use for which a Saccharomyces spp. strain of that species would be used. For example, a strain of Saccharomyces cerevisiae that is capable of utilising xylose as a sole carbon source may be used in baking, brewing, biomass production, sugar fermentation and ethanol production, or any other uses to which standard *Saccharomyces* strain are used.

The ability of the *Saccharomyces* strain of the present invention to grow on xylose as a sole carbon source provides a convenient phenotype that can be used to distinguish between *Saccharomyces* strain which are capable of growth rates of at least one generation per 48 hours using xylose as a sole carbon source, and those that are not for purposes of "marking" yeast strains.

In one aspect, there is provided a method of marking a *Saccharomyces* strain, comprising the steps of:
  (a) culturing the desired strain with a strain of the invention under conditions to permit combining of DNA of the strains;
  (b) selecting or screening for derivatives of the desired strain which have an increased growth rate using xylose as a sole carbon source for growth;
  (c) isolating derivatives of the desired strain which have an increased growth rate using xylose as a sole carbon source for growth.

In one embodiment, the method comprises:
(a) mating the desired strain with a *Saccharomyces* strain of the fourth to fourteenth aspect under conditions which permit combining of DNA of the strains; and
(b) screening or selecting for a derivative of the desired strain that is capable of growing at a rate of greater than one generation per 48 hours using xylose as a sole carbon source by plating the mated cells on xylose-containing solid medium or by culturing in xylose-containing liquid medium or a combination of both;
(c) isolating derivatives of the desired strain which have an increased growth rate using xylose as a sole carbon source for growth.

Marked strains may be detected by incubating the strain on or in xylose-containing minimal media and determining the growth rate, or comparing the growth rate to that of a standard strain with known growth rate on or in xylose-containing medium. A suitable test for detecting a marked strain is Test T1, whereby a marked strain exhibits at least a 2-fold increase in biomass in Test T1.

In another embodiment, the *Saccharomyces* spp. strain of the invention may be used for the production of compounds such as ethanol, xylitol, acetic acid, other yeast byproducts, enzymes, etc. Methods for the production of compounds may comprise the following steps:
(a) cultivating the *Saccharomyces* strain in a xylose-containing medium under conditions which permit the strain to produce the compound; and
(b) recovering the compound(s) that is produced by the strain.

The compounds may be one or more compounds or mixtures thereof that are produced by *Saccharomyces* when utilising xylose as a carbon source. For example, the compound may be ethanol, xylitol, acetic acid, carbon dioxide, or any component, metabolites and byproducts of yeast cells and their metabolism. Components of yeast cells may include enzymes, co-factors, vitamins, amino acids, peptides, proteins, nucleosides, nucleotides, oligonucleotides, DNA, RNA, cell wall components, glucans, mannoproteins, membrane components, lipids, sterols, storage carbohydrates, trehalose, glycogen, organic acids, succinic acid, acetic acid, lactic acid, polyols such as glycerol, xylitol.

It will be appreciated by persons skilled in the art that the type of compounds produced by the *Saccharomyces* spp. strain may depend on the growth conditions to which the strain is subjected. For example, temperature, aerobic or anaerobic growth, pH of the medium, nitrogen source, presence of carbon sources other than xylose, other compounds in the medium on their own or in combination may impact on the types of compounds that are produced by the *Saccharomyces cerevisiae* strain. However, precise conditions for production of any one or more compounds can be readily determined by a person skilled in the art through standard procedures.

It will also be appreciated by persons skilled in the art that the *Saccharomyces* strains of the invention will be capable of utilising sugars such as glucose, fructose, mannose, galactose, maltotriose, maltose, sucrose, melibiose, raffinose, xylose, melizitose, alpha-methyl-glucoside, trehalose, isomaltose. The strains may also be capable of using non-sugar carbon sources such as ethanol, acetate, glycerol, xylitol.

The strain of the invention will typically be capable of fermenting sugars such as glucose, fructose, mannose, galactose, maltotriose, maltose, sucrose, melibiose, raffinose, xylose, melizitose, alpha-methyl-glucoside, trehalose or isomaltose in addition to xylose for production of carbon dioxide and ethanol.

The xylose in the xylose-containing medium may be in any form that can be utilised by the yeast. For example, the xylose may be purified, or it may be in a crude form such as a hemicellulose hydrolysate obtained from acid hydrolysis of biomass such as sugar cane, straw, corn stover, timber products etc.

In the production of biomass and compounds, the inoculated xylose-containing media is typically cultivated at a temperature range of between 22° C. and 40° C. for between 2 hours and 4 days.

The inventors have further found that in order to produce ethanol from xylose using the strains of the invention, it is not necessary that the strains exhibit substantial growth on the xylose. The inventors have found that heavy inocula of xylose-containing medium with strains of the invention results in ethanol production within 2 hours, typically 4 hours, more typically 5 hours. Under such conditions, substantial growth is not detectable. Thus, there is also provided a method of producing ethanol comprising:
  (a) inoculating xylose-containing media with the strain of the first to eighth, twelfth or thirteenth aspects to a density of at least $1 \times 10^8$ yeast cells per ml of media;
  (b) incubating the inoculated media for sufficient time to permit ethanol production;
  (c) recovering the ethanol.

The xylose containing media may be any of the xylose-containing media mentioned above.

The density of yeast cells may be at least $5 \times 10^8$, typically at least $6 \times 10^8$ yeast cells per ml of media.

The inoculated media may be incubated for at least 2 hours, typically at least 5 hours.

In another aspect, there is provided a method of producing ethanol comprising incubating a non-recombinant *Saccharomyces* strain in xylose-containing media under conditions sufficient to produce ethanol and thereafter recovering the ethanol.

Definition of Tests T1 to T9.

T1: Growth Using Xylose as Sole Carbon Source

Yeast strains are streaked onto on Glucose Yeast extract Bacteriological Peptone medium solidified with 2% Agar using standard microbiological techniques. After incubation for 72 hours at 30 degrees Celsius, yeast cells are taken from plates using a sterile microbiological loop and inoculated to an $OD_{600}$ (Optical Density at 600 nm) of between 0.1 and 0.2 units ($OD_{600}$ at $T_0$) in 50 ml of broth. The broth contains xylose (5% w/v), DIFCO® (culture medium) Yeast Nitrogen Base without amino acids (0.67%) in distilled water in a 250 ml Erlenmeyer flask. Cultures are incubated at 30 degrees Celsius with shaking at 220 rpm (10 cm orbital diameter) for 48 hours prior to measuring $OD_{600}$ (OD at $T_{48hrs}$). The fold increase in biomass is determined by the equation:

$$\frac{OD_{600} \text{ at } T_{48hrs}}{OD_{600} \text{ at } T_0}.$$

T2: Cell Biomass Yield Using Xylose as Sole Carbon Source.

Yeast strains are streaked onto on Glucose Yeast extract Bacteriological Peptone medium solidified with 2% Agar using standard microbiological techniques. After incubation for 72 hours at 30 degrees Celsius, yeast cells are taken from plates using a sterile microbiological loop and inoculated to an $OD_{600}$ (Optical Density at 600 nm) of between 0.1 and 0.2 units in 50 ml of broth. The broth contains xylose (5% w/v), DIFCO® (culture medium) Yeast Nitrogen Base without amino acids (0.67%) in distilled water in a 250 ml Erlenmeyer flask. Cultures are incubated at 30 degrees Celsius with shaking at 220 rpm (10 cm orbital diameter) for 72 hours prior to measuring the yield of dry yeast matter. The dry weight content of the yeast is measured by transferring 5 mls of yeast culture to a pre-weighed glass test tube (W1), followed by centrifugation at 3000 g for 10 minutes at 22 degrees C. The supernatant is removed without disturbing the yeast pellet, and the cells are resuspended in 5 ml of distilled water, prior to re-centrifugation at 3000 g for 10 minutes at 22 degrees C. The supernatant is again removed without disturbing the yeast pellet, and the cells are resuspended in 5 ml of distilled water, prior to re-centrifugation at 3000 g for 10 minutes at 22 degrees C. The glass test tube containing the yeast cells is baked at 105 degrees C. for 24 hours and weighed (W2). Dry yeast matter is calculated by subtracting W1 from W2 and multiplying the obtained value by 10. Assays are performed in duplicate and the average is calculated.

T3: Production of Ethanol Using Xylose as Sole Carbon Source.

Inoculum of yeast was prepared by growing 1 standard microbial loopful of pure cells of the strain for 16 hr at 30° C. with shaking at 200 rpm in a 250 mL Erlenmeyer flask containing in 50 mL distilled water: 2.5 g xylose, 0.5 g yeast extract, 0.5 g bacteriological peptone. Seven×50 mL cultures were grown simultaneously. The cultures were harvested by centrifugation at 22° C. and 3,000×g for 5 min. Supernatant was discarded and cell pellets were resuspend in sterile distilled water and re-centrifuged. Supernatant was discarded and cell pellets resuspended and pooled in 20 mL of xylose minimal medium which contained per L of distilled water:

50 g xylose, 13.4 g DIFCO® (culture medium) Yeast Nitrogen Base without amino acids, supplemented with 0.4 mg of $CuSO_4.4H_2O$, 1 mg $ZnSO_4.7H_2O$, 2 mg of $MnSO_4.4H_2O$, 1 mg $Na_2MoO_4.2H_2O$, 1 mg of 20 $Na_2B_4O_7.10H_2O$, 2 mg Ca-pantothenate, 2 mg thiamine HCl, 2 mg pyridoxine HCl, 4 mg inositol, 1 mg nicotinic acid, and 0.4 mg biotin.

The cells were then inoculated into 980 mL of the same xylose minimal medium which had been prewarmed to 30° C. and aerated to 20% oxygen is a Braun Biostat B 2 L fermentation vessel. Yeast was grown with air pumped at 10 L per min, stirring at 1200 rpm and pH maintained at pH 5 using additions of KOH or phosphoric acid as required. After 24 h, 300 mL of the culture volume was removed and replaced with 300 ml fresh xylose minimal medium comprising 50 g xylose plus 10 g DIFCO® (culture medium) Yeast Nitrogen Base without amino acids and trace salts and vitamins in the amounts described above. After a further 7 hours, 30 g of fresh xylose was added to the culture and air supply was reduced to 4 L/min and stirrer speed reduced to 200 rpm. Ethanol was assayed after a further 20 h by use of a YSI 2700 Select Biochemistry Analyzer fitted with a YSI membrane 2786 for ethanol detection (YSI Inc. Yellow Springs, Ohio, USA).

T4: Assay of Xylose Reductase:

Strains of yeast were grown on glucose, yeast extract and bacteriological peptone agar as described previously, were inoculated to an optical density at 600 nm of between 0.1 and 0.2 units in a 250 mL shake flask in 50 mL medium that contained 5% w/v xylose, 0.5% w/v yeast extract and 1% w/v bacteriological peptone (XYP). Cultures were incubated at 30° C. and 180 rpm until they reached optical density at 600 nm of between 3 and 5 units. If cells did not reach the required density after 24 h incubation they were nevertheless harvested. Cells were harvested by centrifugation at 3,000×g and 4° C. for 5 min. The supernatant was discarded and the cell pellet was resuspended in chilled distilled water and re-centrifuged. Supernatant was discarded and the process repeated so as to remove all traces of medium.

Cells were re-suspended in disintegration buffer and cell extracts prepared as described in Eliasson A., et al. (2000) Applied and Environmental Microbiology, volume 66 pages 3381-3386. The cell extracts were then assayed for xylose reductase activities according to the methods described and referred to in Eliasson A., et al. (2000) Applied and Environmental Microbiology, volume 66 pages 3381-3386. One unit of activity is defined as 1 nanomole of NAD(P)H reduced or oxidised per minute per mg of protein at 30° C. Protein was assayed by the method described by Lowry O H, Rosebrough N J, Farr A L, and Randall R J (1951) Journal of Biological Chemistry 193:265-275, using a bovine serum albumin standard.

T5: Assay of Xylitol Dehydrogenase.

Strains of yeast were grown on glucose, yeast extract and bacteriological peptone agar as described previously, were inoculated to an optical density at 600 nm of between 0.1 and 0.2 units in a 250 mL shake flask in 50 mL medium that contained 5% w/v xylose, 0.5% w/v yeast extract and 1% w/v bacteriological peptone (XYP). Cultures were incubated at 30° C. and 180 rpm until they reached optical density at 600 nm of between 3 and 5 units. If cells did not reach the required density after 24 h incubation they were nevertheless harvested. Cells were harvested by centrifugation at 3,000×g and 4° C. for 5 min. The supernatant was discarded and the cell pellet was resuspended in chilled distilled water and re-centrifuged. Supernatant was discarded and the process repeated so as to remove all traces of medium.

Cells were re-suspended in disintegration buffer and cell extracts prepared as described in Eliasson A., et al. (2000) Applied and Environmental Microbiology, volume 66 pages 3381-3386. The cell extracts were then assayed for xylitol dehydrogenase activities according to the methods described and referred to in Eliasson A., et al. (2000) Applied and Environmental Microbiology, volume 66 pages 3381-3386. One unit of activity is defined as 1 nanomole of NAD(P)H reduced or oxidised per minute per mg of protein at 30° C. Protein was assayed by the method described by Lowry O H, Rosebrough N J, Farr A L, and Randall R J (1951) Journal of Biological Chemistry 193:265-275, using a bovine serum albumin standard.

T6: Assay of Xylulose Kinase.

Strains of yeast were grown on glucose, yeast extract and bacteriological peptone agar as described previously, were inoculated to an optical density at 600 nm of between 0.1 and 0.2 units in a 250 mL shake flask in 50 mL medium that contained 5% w/v xylose, 0.5% w/v yeast extract and 1% w/v bacteriological peptone (XYP). Cultures were incubated at 30° C. and 180 rpm until they reached optical density at 600 nm of between 3 and 5 units. If cells did not reach the required density after 24 h incubation they were nevertheless harvested. Cells were harvested by centrifugation at 3,000×g and 4° C. for 5 min. The supernatant was discarded and the cell pellet was resuspended in chilled distilled water and re-centrifuged. Supernatant was discarded and the process repeated so as to remove all traces of medium.

Cells were re-suspended in disintegration buffer and cell extracts prepared as described in Eliasson A., et al. (2000) Applied and Environmental Microbiology, volume 66 pages 3381-3386. The cell extracts were then assayed for xylulose kinase activities according to the methods described and referred to in Eliasson A., et al. (2000) Applied and Environmental Microbiology, volume 66 pages 3381-3386. One unit of activity is defined as 1 nanomole of NAD(P)H reduced or oxidised per minute per mg of protein at 30° C. Protein was assayed by the method described by Lowry O H, Rosebrough N J, Farr A L, and Randall R J (1951) Journal of Biological Chemistry 193:265-275, using a bovine serum albumin standard.

T7: Growth Using Xylitol as Sole Carbon Source

Yeast strains are streaked onto on Glucose Yeast extract Bacteriological Peptone medium solidified with 2% Agar using standard microbiological techniques. After incubation for 72 hours at 30 degrees Celsius, yeast cells are taken from plates using a sterile microbiological loop and inoculated to an $OD_{600}$ (Optical Density at 600 nm) of between 0.1 and 0.2 units ($OD_{600}$ at $T_0$) in 50 ml of broth. The broth contains xylitol (5% w/v), DIFCO® (culture medium) Yeast Nitrogen Base without amino acids (0.67%) in distilled water in a 250 ml Erlenmeyer flask. Cultures are incubated at 30 degrees Celsius with shaking at 220 rpm (10 cm orbital diameter) for 48 hours prior to measuring $OD_{600}$ ($OD_{600}$ at $T_{48hrs}$). The fold increase in biomass is determined by the equation:

$$\frac{OD_{600} \text{ at } T_{48hrs}}{OD_{600} \text{ at } T_0}$$

T8: Ethanol Production Using Xylose in a Rich Medium.

Yeast strains are streaked onto on Glucose, Yeast Extract, Bacteriological Peptone, medium solidified with 2% Agar using standard microbiological techniques. After incubation for 96 hours at 30 deg Celsius, yeast cells are taken from plates using a sterile microbiological loop and inoculated to an $OD_{600}$ (Optical Density at 600 nm) of between 1 and 2 units in 50 ml of broth. The broth contains xylose (5% w/v), Yeast extract (0.5% w/v) and Bacteriological Peptone (1% w/v) in distilled water in a 250 ml Erlenmeyer flask. Cultures are incubated at 30 deg Celsius with shaking at 220 rpm (10 cm orbital diameter). Samples of the culture supernatant are assayed hourly for a period of 24 hours for ethanol by use of a YSI 2700 Select Biochemistry Analyzer fitted with a YSI membrane 2786 for ethanol detection (YSI Inc. Yellow Springs, Ohio, USA). Levels of ethanol are expressed as grams per liter.

T9: Ethanol Production in Xylose Minimal Mineral Medium Under Anaerobic Conditions.

Yeast strains were streaked onto on 5% w/v xylose, 0.67% w/v DIFCO® (culture medium) Yeast Nitrogen Base without amino acids medium solidified with 2% agar using standard microbiological techniques. After incubation for 96 hours at 30 degrees Celsius, yeast cells are taken from plates and inoculated directly into 10 mL of sterile 5% w/v xylose plus 0.67% w/v DIFCO® (culture medium) Yeast Nitrogen Base without amino acids contained in a 15 mL volume sterile PP-Test Tubes (Cellstar, Greiner bio-one) to an optical density at 600 nm of 0.1 to 0.4. Medium was overlayed with 2 mL sterile mineral oil to inhibit oxygen transfer, screw caps fully tightened and tubes were incubated without shaking at 30° C. Samples for ethanol assay were removed using sterile Pasteur pipettes, without disturbing cell pellets that had formed through growth of original inoculum. Ethanol was assayed using a YSI 2700 Select Biochemistry Analyzer fitted with a YSI membrane 2786 for ethanol detection (YSI Inc. Yellow Springs, Ohio, USA).

The invention will now be described in detail by way of reference only to the following non-limiting examples.

EXAMPLE 1

Saccharomyces is Capable of Slow Growth Using Xylose as the Sole Carbon Source.

Baker's yeast Saccharomyces cerevisiae strain NL67 (Higgins et al. (1999) Applied and Environmental Microbiology 65:680-685) was inoculated onto solidified minimal mineral medium with or without xylose as a sole carbon source and incubated at 30° C. for two months. It was observed using a light microscope that microscopic colonies occurred on both types of plates, but that the colonies on the medium containing xylose were detectably larger than those provided with no carbon source. Whereas the cells on medium containing no xylose had progressed through 5 to 6 generations, the cells on medium containing xylose had progressed through 9 to 10 generations.

EXAMPLE 2

Generation of Populations Comprising Diverse Strains of Saccharomyces Capable of Rapid Growth on Xylose as Sole Carbon Source.

By obtaining yeast strains from a variety of sources, which included strains obtained from the wild, from wine, distiller's and beer fermentations, and baking applications, inducing them to sporulate and using mass mating techniques to generate a genetically diverse population it was possible to apply selection pressure to enrich for yeast strains capable of more vigorous growth using xylose as a sole carbon source. By spreading the genetically diverse populations onto xylose minimal mineral medium (and simultaneously onto the same minimal mineral medium without a carbon source) and incubating for two months, it was observed that there was heterogeneity in the colony size. By comparing the plates with xylose and without xylose, the observation was made that contrary to accepted dogma, growth had been due to the addition of xylose to the medium, implying that there was heterogeneity in the ability of the yeast strains within the population to grow on xylose. By harvesting the entire xylose grown population, and sporulating them, it was possible to generate new populations of yeast that were enriched for genetic information conferring ability to grow more effectively on xylose. By using large population sizes (at least 100,000) and pooling cells including those that did not grow optimally, the genetic diversity of the population was maintained in each generation. As the number of cycles of mating and selection increased, the heterogeneity of colony sizes was maintained but the final size of the colonies increased.

After between 5 and twenty cycles of selection on agar plates, the populations were introduced into liquid culture containing minimal mineral medium with xylose as a sole carbon source, and continually sub-cultured for approximately 50 generations. The subsequent populations were sporulated and new populations were constructed by mass-mating. The new populations of heterogeneous Saccharomy-

*ces* cells were grown in liquid culture in xylose minimal medium for approximately 50 generations. After this time some of the sample was stored and some of the sample was sporulated. Germinated spores derived from the selected population were mated en masse to generate a new population of heterogeneous *Saccharomyces cerevisiae* cells to grow under selection pressure in liquid xylose minimal medium for approx. 50 generations. This process can be reiterated until desired growth rates are achieved.

To determine whether growth rates of populations on xylose minimal medium were increasing, samples taken after 365, 569, 1013, 1059, 1170, and 1377 days respectively of selection were inoculated into xylose minimal medium at an optical density of 600 nm (OD) between 0.1 and 0.2 with shaking at 220 rpm and 30 deg C. OD was re-assayed after 24 h and used to calculate average doubling time over the 24 h period according to standard microbiological method. The results were plotted graphically and are shown in FIG. 1.

FIG. 1 shows the improvement in growth rates of the populations en masse is exponential as they progress through rounds of mating and selection for growth on xylose as the sole carbon source. This improvement in growth rate on xylose as sole carbon source is predicted to continue until growth rate on xylose is equivalent to the growth rate on glucose as sole carbon source.

EXAMPLE 3

Ethanol Production in Xylose Rich Medium by Heterogeneous Populations of Non-Recombinant *Saccharomyces* Strains Correlates with Growth Rate on Xylose Minimal Mineral Medium Doubling times of the populations in xylose minimal medium were determined as described in Example 2, FIG. 1. Ethanol production was determined by inoculating samples of populations at an optical density at 600 nm of between 1 and 2 into 250 mL shake flasks at in 50 mL medium that contained 5% w/v xylose, 0.5% w/v yeast extract and 1% w/v bacteriological peptone (XYP). Cultures were incubated at 30° C. and 220 rpm and ethanol production monitored over a 2 day period.

The data obtained (Table 1) indicate that the ability to produce ethanol in xylose rich medium increased as doubling time of heterogeneous populations on xylose minimal medium was reduced. Both characteristics improved in concert with the number of reiterations and length of time that the mating and selection process was applied.

TABLE 1

Ethanolic fermentation of xylose in rich medium improves as growth rate of heterogeneous populations of non-recombinant *Saccharomyces* in xylose minimal mineral medium increases

| Population | Doubling time (h) in xylose minimal medium | Minutes incubation in Xylose rich medium | | | | | |
|---|---|---|---|---|---|---|---|
| | | 1035 min | 1155 min | 1275 min | 1395 min | 1455 min | 2465 min |
| 1 | 142 | 0 | 0 | 0 | 0 | 0 | 0 |
| 2 | 76 | 0 | 0 | 0 | 0 | 0 | 0 |
| 3 | 17 | 0 | 0 | 0 | 0 | 0 | .02 |
| 4 | 14 | 0 | 0 | 0 | 0.01 | 0.01 | 0.02 |
| 5 | 10 | 0 | 0 | 0.06 | 0.09 | 0.12 | 0.69 |
| 6 | 7 | 0.01 | 0.05 | 0.14 | 0.16 | 0.21 | 1.1 |

Numbers for ethanol production represent g ethanol/L produced at the time (min) indicated.

EXAMPLE 4

Characterization of Pure Non-Recombinant Strains of *Saccharomyces* Capable of Growth on Xylose as Sole Carbon Source According to Tests T1 and T2.

*Saccharomyces* strain isolates were purified from xylose-utilising populations of Example 2 by standard microbiological procedure and tested for growth and yields on xylose as sole carbon source according to Test T1 and T2. Strains CEN.PK (Karhumaa et al. (2005) Yeast 22:259-368) and NL67(Higgins et al. (1999) Applied and Environmental Microbiology 65:680-685) were included as representing strain types existing prior to the application of the methods described herein. Strains NM04/41257 and NM04/41258 (deposited) are derived from populations that had gone through 1059 days of running of the protocol described in Example 2 and FIG. 1. Strains ISO 10 (NM 05/45177) and ISO 7 (NM 05/45178) were obtained from populations that had gone through 1377 days, and 1431 days, respectively, of running of the protocol described in Example 2 and FIG. 1. The individual isolated yeast strains were confirmed to be members of the species *Saccharomyces cerevisiae* by sporulation and mating of subsequently derived haploids with known laboratory strains of *Saccharomyces cerevisiae* with genetic markers.

TABLE 2

Growth of pure strains of *Saccharomyces cerevisiae* on xylose minimal medium as described in Test T1.

| STRAIN | Initial Optical Density | Final Optical Density | Fold Increase |
|---|---|---|---|
| CEN.PK | 0.128 | 0.132 | 1.03 |
| NL67 | 0.154 | 0.198 | 1.29 |
| NM04/41257 | 0.111 | 2.57 | 23.15 |
| NM04/41258 | 0.110 | 2.9 | 26.36 |
| ISO 10 NM 05/45177 | 0.127 | 6.3 | 49.61 |
| ISO 7 NM 05/45178 | 0.170 | 6.8 | 40 |

Biomass yields of pure strains of *Saccharomyces cerevisiae* on xylose minimal medium were assayed as described in Test T2. Strains CEN.PK and NL67 were again included as representing strain types that have not been generated using the methods described herein. CEN.PK yield=1 mg dry yeast matter per 50 mL culture; NL67 yield=2 mg dry yeast matter per 50 mL culture; NM04/41257 yield=50 mg dry yeast matter per 50 mL culture; NM04/41258 yield=55 mg dry yeast matter per 50 mL culture; ISO 10 yield=145 mg dry yeast matter per 50 mL culture, ISO 7 yield=114 mg dry yeast matter per 50 mL culture.

The above data indicate that the protocol generates strains that possess the ability to rapidly grow and yield well using xylose as a sole carbon source. Taken with the populations data in Example 2 and FIG. 1 the data demonstrate that the protocol can be applied reiteratively to derive strains that have a maximum possible growth rate and yield on xylose, which could be equivalent to growth rate and yield on glucose.

EXAMPLE 5

Non-Recombinant *Saccharomyces* Strains Capable of Rapid Growth and of Producing Ethanol Using Xylose as the Sole Carbon Source.

Inoculum of strain ISO10 was prepared by growing 1 standard microbial loopful of pure cells of the strain for 16 hr at 30° C. with shaking at 200 rpm in a 250 mL Erlenmeyer flask containing in 50 mL distilled water, 2.5 g xylose, 0.5 g yeast extract, and 0.5 g bacteriological peptone. Seven×50 mL cultures were grown simultaneously. The cultures were harvested by centrifugation at 22° C. and 3,000×g for 5 min. Supernatant was discarded and cell pellets were resuspended in sterile distilled water and re-centrifuged. Supernatant was discarded and cell pellets re-suspended and pooled in 20 mL of xylose minimal medium which contained per L of distilled water: 50 g xylose, 13.4 g DIFCO® (culture medium) Yeast Nitrogen Base without amino acids, supplemented with 0.4 mg of $CuSO_4.5H_2O$, 1 mg $ZnSO_4.7H_2O$, 2 mg of $MnSO_4.4H_2O$, 1 mg $Na_2MoO_4.2H_2O$, 1 mg of $Na2B_4O_7.10H_2O$, 2 mg Ca-pantothenate, 2 mg thiamine HCl, 2 mg pyridoxine HCl, 4 mg inositol, 1 mg nicotinic acid, and 0.4 mg biotin.

The cells were then inoculated into 980 mL of the same xylose minimal medium which had been pre-warmed to 30° C. and aerated to 20% oxygen in a Braun Biostat B 2 L fermentation vessel. Yeast was grown with air pumped at 10 L per min, stirring at 1200 rpm and pH maintained at pH 5 using additions of KOH or phosphoric acid as required. After 24 h, 300 mL of the culture volume was removed and replaced with 300 ml fresh xylose minimal medium comprising 50 g xylose plus 10 g DIFCO® (culture medium) Yeast Nitrogen Base without amino acids and trace salts and vitamins in the amounts described above. This gave a culture of cell mass of 4 g dry yeast equivalents per L. Aeration and stirring was maintained at 10L/min and 1200 rpm, respectively and pH was maintained at pH 5. Under these conditions yeast biomass doubled in 4 hours (based on dry yeast matter) with a yield of 4 g dry yeast matter from 10 g consumed xylose.

When yeast grown by the procedure described above reached a density of about 12 g (dry yeast equivalent) per L, 30 g of fresh xylose was added to the culture and air supply was reduced to 4 L/min and stirrer speed reduced to 200 rpm. Under these conditions where dissolved oxygen was undetectable, 17 g of xylose was consumed and a further 1 g dry yeast matter was produced along with 1.75 g ethanol/L and 1 g xylitol/L in 20 h.

EXAMPLE 6

Activities of Xylose Reductase (XR), Xylitol Dehydrogenase (XDH) and Xylulokinase (XK) in Exponentially Growing Non-Recombinant Yeast Strains.

Strains of yeast were grown on glucose, yeast extract and bacteriological peptone agar as described in test T1, were inoculated to an optical density at 600 nm of between 0.1 and 0.2 units in a 250 mL shake flask in 50 mL medium that contained 5% w/v xylose, 0.5% w/v yeast extract and 1% w/v bacteriological peptone (XYP). Cultures were incubated at 30° C. and 180 rpm until they reached optical density at 600 nm of between 3 and 5 units. If, as in the case of strains such as NL67 and CEN.PK, cells did not reach the required density after 24 h incubation they were nevertheless harvested and assayed. Cells were harvested by centrifugation at 3,000×g and 4° C. for 5 min. The supernatant was discarded and the cell pellet was resuspended in chilled distilled water and re-centrifuged. Supernatant was discarded and the process repeated so as to remove all traces of medium.

Cells were re-suspended in disintegration buffer and cell extracts prepared as described in Eliasson A., et al. (2000) Applied and Environmental Microbiology, volume 66 pages 3381-3386. The cell extracts were then assayed for XR, XDH and XK activities according to the methods described and referred to in Eliasson A., et al. (2000) Applied and Environmental Microbiology, volume 66 pages 3381-3386. The following activities were found where one unit of activity is defined as 1 nanomole of NAD(P)H reduced or oxidised per minute per mg of protein at 30° C.

TABLE 3

Units of enzyme activities of yeast strains

| Strain | XR Activity | XDH Activity | XK Activity |
|---|---|---|---|
| CEN.PK | 0.74 | 0.025 | 23 |
| NL67 | 0.74 | 0.12 | 20.2 |
| NM04/41257 | 1.16 | 1.09 | 20.9 |
| NM04/41258 | 1.61 | 1.13 | 22.5 |
| ISO 10 | 3.81 | 8.09 | 22.5 |
| ISO 7 | 5.39 | 13.35 | 29.75 |

These data suggest that the reiterative mating and selection methodology applied to obtain the yeasts that grow on xylose as the sole carbon source has resulted in improved XR and XDH activities that are critical for metabolism of xylose and xylitol.

It is likely that other enzymes and activities such as those involved in pentose phosphate pathway have also been naturally improved in our strains due to the selective pressures applied in the breeding and selection procedures. Those skilled in the art would realize that our strains could obviously be used as a basis for further improvement using further selections and combinations of breeding, mutagenesis, protoplast fusion, cytoduction and/or recombinant DNA techniques that optimize activities of XR, XDH, XK, or introduce and optimize xylose isomerase, or other genetic changes required to improve xylose, xylitol and xylulose metabolism.

EXAMPLE 7

Characterization of Pure Non-Recombinant Strains of *Saccharomyces* Capable of Growth on Xylitol as Sole Carbon Source According to Test T7.

Pure strains were grown on glucose, yeast extract and bacteriological peptone agar as described in test T1. Colonies of the strain were inoculated in to 50 mL of 5% w/v xylitol plus 0.67% DIFCO® (culture medium) Yeast Nitrogen Base without Amino Acids and tested for growth as described in Test T7.

TABLE 4

Growth of pure strains of *Saccharomyces cerevisiae* on xylitol minimal medium as described in Test T7.

| STRAIN | Initial Optical Density | Final Optical Density | Fold Increase |
|---|---|---|---|
| CEN.PK | 0.146 | 0.130 | 0.89 |
| NL67 | 0.156 | 0.164 | 1.05 |
| NM04/41257 | 0.130 | 0.171 | 1.32 |
| NM04/41258 | 0.105 | 3.03 | 28.86 |
| ISO 10 | 0.108 | 0.115 | 1.065 |
| ISO 7 | 0.198 | 6.96 | 35.15 |

These data suggest that the reiterative mating and selection methodology applied to obtain the yeasts that grow on xylose as the sole carbon source has resulted in some strains that can also utilize xylitol as the sole carbon source.

EXAMPLE 8

Production of Ethanol Using Xylose Rich Medium by Pure Non-Recombinant Strains of *Saccharomyces* Capable of Growth on Xylose as Sole Carbon Source According to Test T8.

Pure isolates of yeasts grown on glucose, yeast extract and bacteriological peptone agar as described in test T1, were inoculated to an optical density at 600 nm of between 1 and 2 units in a 250 mL shake flask in 50 mL medium that contained 5% w/v xylose, 0.5% w/v yeast extract and 1% w/v bacteriological peptone (XYP) and assayed as described in Test T8.

TABLE 5

Ethanol production using xylose rich medium

| STRAIN | Initial Optical Density | Optical Density after 24 h | Ethanol (g/L) after 24 h |
| --- | --- | --- | --- |
| CEN.PK | 1.16 | 1.9 | 0 |
| NL67 | 1.29 | 1.8 | 0 |
| NM04/41257 | 1.06 | 14.5 | 0.04 |
| NM04/41258 | 1.17 | 17.2 | 0.07 |
| ISO 10 | 1.18 | 20.0 | 0.66 |
| ISO 7 | 1.15 | 21.2 | 1.32 |

These data show that the selection strategy based on growth of yeasts on xylose as the sole carbon source generates yeast strains that are capable of producing ethanol from xylose. These data coupled with data of Example 3 (Table 1), show that the ability to grow and yield cell biomass using xylose as the sole carbon sugar increases in concert with increasing ability to produce ethanol from xylose. Moreover strains such as NM04/41258 and ISO 7 that can utilize xylitol and xylose are able to produce ethanol. The finding that strains NM04/41258 and ISO 7 (NM 05/45178) which can utilize xylitol and make ethanol from xylose goes against the teaching of U.S. Pat. No. 4,511,656, which states strains should be screened to isolate the specific colony or colonies which will utilize D-xylose but not xylitol.

EXAMPLE 9

Isolation and Characterisation of Pure Non-Recombinant Strains of *Saccharomyces* Capable of Ethanol Production Using Xylose as Sole Carbon Source Under Anaerobic Conditions.

Isolates were purified from xylose-utilising populations that had undergone 1106 days of selection and were subjected to Test T9. Fifty individual isolates were tested and ethanol production assayed after three weeks to 4 months ranged from 0.24 g/L to 0.75 g/L. Strains NM04/41257 and NM04/41258 were also included in these assays.

TABLE 6

Production of ethanol by pure yeast strains in xylose minimal medium under anaerobic conditions.

| Strain | Incubation Period | g/L Ethanol Produced |
| --- | --- | --- |
| NM04/41257 | 4 months | 0.82 |
| NM04/41258 | 4 months | 0.48 |
| Isolate no. 2 | 1 month | 0.70 |
| Isolate no. 6 | 1 month | 0.75 |
| Isolate no. 21 | 1 month | 0.70 |
| Isolate no. 23 | 1 month | 0.73 |
| Isolate no. 31 | 3 weeks | 0.64 |
| Isolate no. 36 | 3 weeks | 0.63 |
| Isolate no. 37 | 3 weeks | 0.65 |

These data indicate that it is possible to obtain non-recombinant *Saccharomyces* yeasts that are capable of fermenting xylose under anaerobic conditions to produce ethanol. The NM04/41257 and NM04/41258 strains were purified from earlier selected populations relative to the other strains in the Table. This data shows that the reiterative protocol described herein results in increased efficiency of anaerobic ethanol production by non-recombinant strains.

EXAMPLE 10

Rapid Ethanol Production by Non-Recombinant *Saccharomyces* Inoculated at High Density into Minimal Media Under Aerobic Conditions.

Strain ISO 10 grown on glucose, yeast extract, bacteriological peptone agar (as described above) was inoculated into 50 mL of 5% w/v xylose, 0.5% w/v yeast extract and 1% w/v bacteriological peptone (XYP) contained in 250 mL Erlenmeyer flasks and incubated for 72 h at 30° C. and 220 rpm. Twenty flasks were incubated simultaneously. Cells were harvested by centrifugation at 3,000×g and 22° C. for 10 min. Supernatant was discarded and cell pellet re-suspended in 10 mL sterile water before re-centrifugation. The supernatant was again discarded and the cells re-suspended in distilled sterile water before a further centrifugation. Finally, cells were re-suspended in 20 mL sterile distilled water.

Fermentation medium was, prepared and filter-sterilized as follows: YNB contained 0.67% DIFCO® (culture medium) Yeast Nitrogen Base without amino acids; XYNB was YNB plus 5% xylose; and GXYNB was YNB plus 0.5% glucose and 4.5% xylose. Media were contained in 125 mL conical glass flasks. They were inoculated with 3 mL of cell suspension and placed on a 220 rpm orbital shaker at 30° C. and ethanol production read at hourly intervals as described previously. Immediately after inoculation optical densities at 600 nm of cultures were measured and it was determined that cell densities for cultures were at 5.7 to 6.1×10e8 per mL.

TABLE 7

Production of ethanol by high density inoculum of Non-recombinant *Saccharomyces* cells.

| Medium | 1 h | 2 h | 3 h | 4 h | 5 h |
| --- | --- | --- | --- | --- | --- |
| YNB | 0.41 | 0.44 | 0.36 | 0.29 | 0.09 |
| XYNB | 0.75 | 1.1 | 1.67 | 2.1 | 2.9 |
| GXYNB | 1.69 | 2.2 | 2.41 | 3.2 | 3.8 |

Numbers refer to g ethanol per L in culture supernatant at the indicated time after inoculation. The small amount of ethanol produced by cells incubated in YNB without a carbon source was derived most likely from carry over of endogenous storage sugars synthesized and accumulated by the yeast during the 72 h inoculum preparation phase. Decline in the ethanol concentration of YNB cultures after 3 h indicates that storage sugars were exhausted or becoming exhausted and ethanol was being consumed by cells and/or ethanol was evaporating.

These data show that it is possible for non-recombinant strains of *Saccharomyces* to be obtained that can ferment xylose rapidly to produce ethanol in minimal medium where xylose is the sole carbon source. Moreover, these strains are able to produce ethanol from xylose in medium where fermentable hexose sugar such as glucose was also added since the ethanol produced by 4 h in GXYNB was in excess of that expected solely from the glucose present.

EXAMPLE 11

Non-Recombinant *Saccharomyces* Biomass Grown on Xylose as the Sole Carbon Source Exhibits Broad Industrially Useful Features.

Those skilled in the art will know that yeasts have proven industrial utility in various fermentation applications (e.g. bread, and ethanol (potable and non-potable) production) and also as a source of amino acids and protein, nucleotides (e.g. DNA and RNA), enzymes (e.g. invertase and phytase), anti-oxidants (e.g. glutathione) and other cellular components such as cell wall components (e.g. glucans). The aforementioned properties are by way of example and are not meant to be limiting.

It would be useful if yeasts could be grown on media that contain xylose and then subsequently used for the various industrial purposes. Therefore, by way of example strain ISO10 was tested for various features following growth on xylose.

Strain ISO10 was grown in per Liter: 50 g xylose, 13.4 g DIFCO® (culture medium) Yeast Nitrogen Base without amino acids, supplemented with 0.4 mg of $CuSO_4.5H_2O$, 1 mg $ZnSO_4.7H_2O$, 2 mg of $MnSO_4.4H_2O$, 1 mg $Na_2MoO_4.2H_2O$, 1 mg of $Na_2B_4O_7.10H_2O$, 2 mg Ca-pantothenate, 2 mg thiamine HCl, 2 mg pyridoxine HCl, 4 mg inositol, 1 mg nicotinic acid, and 0.4 mg biotin. Cells were stirred at 1200 rpm with air supply at 12 L per min and temperature at 30° C. and pH maintained at pH 5 using 1M KOH and 1M phosphoric acid. When cell density was at $A_{600}$, cells were harvested by centrifugation at 3,000×g and 22° C. for 10 min. Cell pellet was resuspended in distilled water and recentrifuged. This washing procedure was carried out three-times and the biomass placed on Whatman filter paper no. 1 to achieve a wet biomass of 22 to 25% solids.

The biomass was assayed for the following features by way of demonstrating that it is possible to grow non-recombinant *Saccharomyces* on xylose as sole carbon source to obtain yeast biomass with properties generally relevant to industrial applications.

Ethanolic fermentation power. Yeast was inoculated into a molasses-based medium to test for ethanolic fermentation power, defined as the ability to produce ethanol from fermentable sugars such as sucrose, glucose and fructose. Sugar cane molasses was diluted in water and sterilized by heating to 121° C. for 5 min. When cooled to 22° C., the molasses was centrifuged at 4,000×g at 22° C. for 10 min to remove solids. The supernatant was diluted to a final concentration of 18% w/w sucrose equivalents and supplemented with filter-sterilised DIFCO® (culture medium) Yeast Nitrogen Base at 0.67% w/v. Forty mL of this medium was inoculated with an equivalent of 6.8 mg dry yeast matter and incubated at 30° C. without shaking Ethanol was assayed at 24 h intervals by use of a YSI 2700 Select Biochemistry Analyzer fitted with a YSI membrane 2786 for ethanol detection (YSI Inc. Yellow Springs, Ohio, USA). After 24 h the yeast produced 16.8 g ethanol per L, and after 1 week the yeast had produced 59 g ethanol per L.

Leavening of bread dough. To test for leavening power, defined as the ability to ferment sugars such as glucose, fructose and maltose and thereby produce carbon dioxide which raises a flour dough, the yeast was added to a bread dough mixture and tested for its ability to produce leavened bread. A dough was prepared that contained 500 g wholemeal flour soy and linseed bread mix (Kitchen Collection, Christchurch), 300 mL tap water and 10 g yeast (at 24% solids). Dough was leavened and baked using a Breville Bakers Oven on setting 3B (HWI Electrical, Sydney Australia). The yeast raised (leavened) the dough mixture to produce a loaf of bread with height of 14 cm.

Glucan content. An amount of yeast biomass equivalent to 59 mg dry matter was extracted for glucans according to the method described by Sutherland I W, and Wilkinson J F (1971) "Chemical Extraction Methods of Microbial Cells", in Methods in Microbiology Vol 5B (Eds. J R Norris and D W Ribbons), Chapter IV pp. 345-383, Academic Press London and New York. According to Sutherland et al. this method produces "cell wall glucan which is free from contaminating material". Using the described procedure an amount of 8 mg of glucan was obtained from the dry yeast starting material.

Amino Acid/Protein content. An amount of yeast material equivalent to 24.6 mg dry yeast matter was suspended in a glass test tube in 2.5 mL of 1 M NaOH and placed in a boiling water bath for 15 min. The boiled sample was cooled to 22° C. and volume made to 10 mL using distilled water. Amino acid/protein was assayed according to Lowry OH, Rosebrough NJ, Farr AL, and Randall RJ (1951) Journal of Biological Chemistry 193:265-275, using a bovine serum albumin standard. This assay indicated the yeast contained equivalent of 39% amino acid/protein material per wt dry matter.

Nucleotide content. An amount of yeast material equivalent 8.3 mg of dry yeast was resuspended in 1 mL of 4% w/v NaCl and autoclaved at 121° C. for 15 min. Upon cooling to 22° C. the yeast suspension was centrifuged at 3,000×g for 10 min at 22° C. and the supernatant assayed for nucleotide content by the spectrophotometric UV absorbance method described by Herbert D, Phipps P J, and Strange R E (1971) "Chemical Analysis of Microbial Cells", in Methods in Microbiology Vol 5B (Eds. J R Norris and D W Ribbons), Chapter III pp. 209-344, Academic Press London and New York. The yeast contained 1.9% nucleotide material per wt dry matter.

Glutathione content. An amount of yeast material equivalent 6.82 mg of dry yeast was resuspended in 0.8 mL of 80:20 ethanol:distilled water, vortex mixed and centrifuged at 10,000×g for 2 min at 22° C. The supernatant was assayed as follows: Phosphate buffer contained 3.99 g $Na_2HPO_4$, 0.43 g $NaH_2PO_4.H_2O$, 0.59 g disodium-EDTA.$2H_2O$ per 250 mL at pH7.5. NADPH solution contained 26.6 mg NADPH tetrasodium salt in 100 mL of phosphate buffer. 5,5"-dithio-bis(2-nitrobenzoic acid) (DTNB) was prepared by weighing 23.8 mg DTNB in 10 mL of phosphate buffer. Glutathione standard was prepared in distilled water to a stock concentration of 0.1 mM. Glutathione reductase stock solution from Fluka Chemie AG contained 162.72 units of activity per mL.

Assay was carried out in a 3 mL spectrophotometer cuvette which contained 1.4 mL of NADPH solution+200 microliter DTNB solution+10 microliter of sample, standard GSH solution, or distilled water and 390 microliter of distilled water. Sample was prewarmed to 30° C. and reaction started by addition of three microliter of glutathione reductase. Cuvettes were incubated at 30° C. for 30 min then the absorbance read against the distilled water blank at 412 nm wavelength using a Shimadzu UV-1201 spectrophotometer. This assay indicated the yeast contained 0.36% total glutathione per wt dry matter.

Phytase activity. An amount of yeast material equivalent to 13.5 mg dry yeast was resuspended in 0.5 mL 0.2M sodium acetate buffer at pH4.9. Phosphatase substrate from Sigma-Aldrich Chemie GmbH was made to 1 mg per mL in 0.2M sodium acetate buffer at pH4.9, and Phytase enzyme from Sigma-Aldrich Chemie GmbH (defined by the supplier as having 1.1 units of phytase activity per mg solid material) was made to 0.909 units per mL in 0.2M sodium acetate buffer at pH4.9. Assay was performed in a cuvette containing 500 microliter of sodium acetate buffer+250 microliter of phosphatase substrate solution and 250 microliter of either yeast suspension, phytase enzyme or distilled water. Cuvettes were incubated for 20 min at 30° C. at which time 300 microliter of 10M NaOH was added. Absorbance at 405 nm was read against the distilled water blank. The phytase activity of the yeast was 0.068 units per mg dry yeast matter.

Invertase activity. An amount of yeast material equivalent to 14.48 mg dry yeast was resuspended in 1 mL of distilled water. The suspension was further diluted one hundred-fold in distilled water. Invertase activity was assayed according to the colorimetric method described in described in test T3 of U.S. Pat. Nos. 4,396,632 and 5,741,695. The yeast produced 0.93 units of invertase activity where a unit of activity is defined as 1 micromole of glucose released from sucrose per minute at 30° C. and pH4.9 per mg of dry yeast.

These data indicate the potential for non-recombinant *Saccharomyces cerevisiae* to be grown on xylose as the sole carbon source to produce biomass, metabolism, cellular components, and/or enzyme activities that are relevant to broad types of industrial applications. Those skilled in the art will know that the exact levels or amounts of these features can be manipulated not only through classical and recombinant genetical methods but also through means of altering culturing conditions, such that the results given above are merely indicative.

The invention claimed is:

1. A method of producing yeast biomass, the method comprising:
    (a) providing strain NM05/45177 or a non-recombinant *Saccharomyces cerevisiae* strain that produces an increase in biomass under the conditions specified in Test T1 that is in the range of from a 2-fold increase in biomass to an increase that is the same as the increase in biomass produced by strain NM05/45177 under the conditions specified in Test T1; and
    (b) growing the strain on or in a medium for growth, wherein the medium comprises xylose as a carbon source.

2. The method of claim 1, wherein the yeast biomass is produced using xylose as a carbon source.

3. The method of claim 1, wherein the *Saccharomyces cerevisiae* strain is NM04/41257.

4. The method of claim 1, wherein the *Saccharomyces cerevisiae* strain is NM04/41258.

5. The method of claim 1, wherein the *Saccharomyces cerevisiae* strain is NM05/45177.

6. The method of claim 1, wherein the *Saccharomyces cerevisiae* strain is NM05/45178.

7. The method of claim 1, wherein the strain is grown aerobically on or in the medium for growth.

8. The method of claim 1, further comprising the step of:
    (c) collecting the biomass produced.

9. The method of claim 8, further comprising the step of:
    (d) recovering a compound from the biomass.

10. The method of claim 9, wherein the compound is ethanol, xylitol, acetic acid, carbon dioxide, an enzyme, a co-factor, a vitamin, an amino acid, a peptide, glutathione, a protein, a nucleoside, a nucleotide, an oligonucleotide, DNA, RNA, a cell wall component, a glucan, a mannoprotein, a membrane component, a lipid, a sterol, a storage carbohydrate, trehalose, glycogen, an organic acid, succinic acid, lactic acid, or a polyol.

11. The method of claim 8, wherein the biomass produced is used in the manufacture of a product selected from the group consisting of bread, beer, potable spirits, fuel ethanol, wine, and food.

12. A method of producing yeast biomass, the method comprising:
    (a) providing an isolated non-recombinant *Saccharomyces cerevisiae* strain that produces at least a 2-fold increase in biomass when grown under the conditions specified in Test T1; and
    (b) growing the strain on or in a medium for growth.

13. The method of claim 12, wherein the medium for growth is a xylose-containing medium, and wherein at least a portion of the yeast biomass is produced using xylose as a carbon source.

14. The method of claim 12, wherein the strain is grown aerobically on or in the medium for growth.

15. The method of claim 12, further comprising the step of:
    (c) collecting the biomass produced.

16. The method of claim 15, further comprising the step of:
    (d) recovering a compound from the biomass.

17. The method of claim 16, wherein the compound is ethanol, xylitol, acetic acid, carbon dioxide, an enzyme, a co-factor, a vitamin, an amino acid, a peptide, glutathione, a protein, a nucleoside, a nucleotide, an oligonucleotide, DNA, RNA, a cell wall component, a glucan, a mannoprotein, a membrane component, a lipid, a sterol, a storage carbohydrate, trehalose, glycogen, an organic acid, succinic acid, lactic acid, or a polyol.

18. The method of claim 15, wherein the biomass produced is used in the manufacture of a product selected from the group consisting of bread, beer, potable spirits, fuel ethanol, wine, and food.

* * * * *